United States Patent
Li

(10) Patent No.: US 11,149,277 B2
(45) Date of Patent: Oct. 19, 2021

(54) METHOD OF PRODUCING ENRICHED EXOSOMES

(71) Applicant: National Health Research Institutes, Miaoli County (TW)

(72) Inventor: Hua-Jung Li, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 15/645,145

(22) Filed: Jul. 10, 2017

(65) Prior Publication Data

US 2018/0010133 A1 Jan. 11, 2018

(30) Foreign Application Priority Data

Jul. 11, 2016 (TW) .................................. 105121824

(51) Int. Cl.
*A61K 31/4035* (2006.01)
*C12N 15/113* (2010.01)
*C12N 5/071* (2010.01)

(52) U.S. Cl.
CPC ...... *C12N 15/1138* (2013.01); *A61K 31/4035* (2013.01); *C12N 5/0631* (2013.01); *C12N 2310/14* (2013.01); *C12N 2310/531* (2013.01); *C12N 2501/02* (2013.01)

(58) Field of Classification Search
None
See application file for complete search history.

(56) References Cited

FOREIGN PATENT DOCUMENTS

WO  WO-2009105044 A1 * 8/2009 ............. A61K 35/12
WO  WO 2013/150303    10/2013

OTHER PUBLICATIONS

Zhu et al (Stem Cells. 2014 ; 32(1): 116-125) (Year: 2014).*
Liu et al (Stem Cells 2016;34: 2943-2955) (Year: 2016).*
Ikushima et al ((Blood. 2013; 121(11):1995-2007)) (Year: 2007).*
Ma, (Sixth Annual Cancer Biology Research Retreat, p. 1-35, Abstact# 37. The Prostaglandin E Receptor EP4 is Upregulated on Breast Cancer Stem-like Cells and Regulates Sensitivity to Natural Killer Cells, 2015) (Year: 2015).*
Dragovic et al, (Nanomedicine: Nanotechnology, Biology, and Medicine, 7: 780-788, 2011) (Year: 2011).*
Lai et al, (J Lipid Res, 60(2):318-322, 2019) (Year: 2019).*
Trach et al, (Phil. Trans. R. Soc. B 373, p. 1-9, 2018) (Year: 2018).*
Hong (Stem Cell Research and Therapy, 10(242); 1-12, 2019) (Year: 2019).*
Brevini et al., 2010, Theriogenology, vol. 74, pp. 544-550 (Year: 2010).*
Paris et al. (2010, Theriogenology, vol. 74, pp. 516-524 (Year: 2010).*
Munoz et al. (2009) Stem Cell Rev. and Rep., vol. 5, 6-9, (Year: 2009).*
Ludwig (Int. J. Mol. Sci. 2019, 20, 4684) (Year: 2019).*
Goessling, et al., "Genetic Interaction of PGE2 and Wnt Signaling Regulates Developmental Specification of Stem Cells and Regeneration", Cell 136, 1136-1147, Mar. 20, 2009.
Mroue, et al., "Three-Dimensional Cultures of Mouse Mammary Epithelial Cells", Methods Mol Biol. 2013 ; 945: 221-250.
Porter, et al., "Prostaglandin E2 Increases Hematopoietic Stem Cell Survival and Accelerates Hematopoietic Recovery After Radiation Injury", Stem Cells 2013;31:372-383.
Simons, et al., "Exosomes—vesicular carriers for intercellular communication", Current Opinion in Cell Biology 2009, 21:575-581.
Skog, et al., "Glioblastoma microvesicles transport RNA and proteins that promote tumour growth and provide diagnostic Biomarkers" Nature Cell Biology vol. 10, No. 12, 2008.
Valadi, et al., "Exosome-mediated transfer of mRNAs and microRNAs is a novel mechanism of genetic exchange between cells", Nature Cell Biology, vol. 9, No. 6, 2007.
Van Niel, et al., "Intestinal Epithelial Cells Secrete Exosome-like Vesicles", Gastroenterology 2001;121:337-349.

* cited by examiner

*Primary Examiner* — Anoop K Singh
*Assistant Examiner* — Magdalene K Sgagias
(74) *Attorney, Agent, or Firm* — Cesari & McKenna, LLP

(57) ABSTRACT

A method of producing induced exosomes, the method comprising: contacting an isolated population of stem cells with an amount of a prostaglandin E receptor 4 (EP4) antagonist effective for inducing release of exosomes, whereby induced exosomes are released from the stem cells, and isolating the induced exosomes.

9 Claims, 35 Drawing Sheets

A

B

A

B

A

B

METHOD OF PRODUCING ENRICHED EXOSOMES

REFERENCE TO RELATED APPLICATION

This application claims priority to Taiwanese Application No. 105121824, filed on Jul. 11, 2016, the entire content of which is hereby incorporated herein by reference.

BACKGROUND

Exosomes can mediate intercellular communication by transferring membrane and cytosolic proteins, lipids, and RNAs between cells (Simons and Raposo, Curr opin Cell Biol 2009; 21:575-581). These transferred molecules can be functional in the recipient cells (Skog et al., Nat Cell Biol 2008; 10:1470-1476; Valadi et al., Nat Cell Biol 2007; 9:654-659). However, although exosome-mediated communication has been shown to be involved in antigen presentation and development of tolerance and tumor progression, the function and regulation of exosomes are still poorly understood.

WO2013150303 A1 discloses exosomes isolated from a cultured neural stem cell line (NSCL), which could increase the fibroblast migration, HUVEC branching and neurite outgrowth. WO2013150303 A1 discloses that the NSCL exosomes were collected from the NSCL in a "basal culture condition," which could maintain stem cell homeostasis of the NSCL. WO2013150303 A1 only provides in vitro data showing that the NSCL exosomes increased fibroblast migration, HUVEC branching, and neurite outgrowth of PC-12 cell line. There is no data showing any effect of NSCL exosomes on modulating the non-stem cell states of PC-12 cells or non-stem cells, improving in vivo nerve repair, or promoting brain memory and cognition.

A variety of observations have pointed to the key role of prostaglandin E2 (PGE2) in maintaining cells in the stem-cell (SC) or cancer stem cell (CSC) states. In the bone marrow, PGE2 signaling supports hematopoietic stem cells (HSCs) (Goessling et al., Cell 2009; 136:1136-1147; Porter et al., Stem Cells 2013; 31: 372-383). Regeneration of the hematopoietic lineage is impaired in mice lacking cyclooxygenase-2 (COX-2), a key enzyme in PGE2 biosynthesis. Similarly, in zebrafish, PGE2 regulates self-renewal of HSCs. However, evidence showing that PGE2 signaling contributes to SC/CSC function in tissues outside of the hematopoietic system has been elusive.

SUMMARY

In one aspect, described herein is a method of producing induced exosomes, the method comprising: contacting an isolated population of stem cells with an amount of a prostaglandin E receptor 4 (EP4) antagonist effective for inducing release of exosomes, whereby induced exosomes are released from the stem cells, and isolating the induced exosomes.

In some embodiment, the contacting step is carried out by culturing the stem cells in a culture medium containing the EP4 antagonist for a sufficient period of time to allow release of the induced exosomes. For example, the stem cells can be cultured for 4 to 8 days.

In some embodiments, the EP4 antagonist is selected from the group consisting of an anti-PGE2 antibody, an siRNA against EP4, an shRNA against EP4, a COX-2 antagonist, a mPGES-1 antagonist, GW627368x, AH23848, L-161,982, CJ-023,423, ONO AE3 208, BGC 20-1531 hydrochloride, MF498, and CJ-42794. An effective amount of the EP4 antagonist used in the method can be 1.0-40 µg/ml.

Stem cells used to produce exosomes can be selected from embryonic stem cells, induced pluripotent stem cells, cancer stem cells, mesenchymal stem cells, hematopoietic stem cells, mammary stem cells, neural stem cells, small intestinal stem cells, skin stem cells, umbilical cord blood stem cells, limbal stem cells, hair follicle stem cells, adipose tissue derived stem cells, bone marrow stem cells, corneal stem cells, and ovarian stem cells.

In some embodiments, the induced exosomes can be isolated by centrifuging, e.g., ultra-centrifuging or sequential centrifuging, the culture medium containing the stem cells to obtain a pellet that includes the induced exosomes.

In another aspect, described herein is a composition containing the induced exosomes produced by stem cells using the method described herein. In some embodiments, the composition is cell-free. The composition can further contain a physiologically acceptable excipient.

In some embodiments, the induced exosomes have one or more of the following properties: (1) a diameter of 50 nm to 150 nm; (2) a higher level of, as compared to exosomes released from control stem cells, one or more of CD44, CD90, integrin β1, integrin α6, CD81, GAPDH, N-cadherin, fibronection, CD146, CD91, cofilin, filamin A, CNP, talin, tropomyosin, galectin 3, Rap1, β-catenin, TGFβ-R1, TGFβ-R2, LRP6, Ago1, Ago2, FZD5, EGFR, HER2, Met, EP2, PI3K, PDK1, Akt, p-Akt, c-Src, p-Src, SAPK/JNK, PSA, VCAM1, VEGFR2, VEGFR3, PDGFβ, NGFR, IL-2Rβ, IL-18Rβ, BMP-7, MIP-3α, RANTES, DR6, LIF, BDNF, TIMP1, VEGFa, and IL-10; (3) a lower level of E-cadherin as compared to exosomes released from the control stem cells; (4) a higher small RNA content as compared to exosomes released from the control stem cells; (5) a higher level of, as compared to exosomes released from control stem cells, one or more of mir-17-92, mir-106a-363, mir-106b-25 clusters, mir-24, mir-130, mir-17, mir-18a, mir-20a, mir-20b, mir-24, mir-25, mir-29a, mir-106b, mir-130a, and mir-130b; (6) a higher level of lipid raft-associated proteins as compared to exosomes released from the control stem cells; and (7) a higher cytokine content as compared to exosomes released from the control stem cells; wherein the control stem cells are stem cells not treated with an EP4 antagonist.

In some embodiments, the induced exosomes in the composition are released from mesenchymal stem cells, mammary epithelial stem cells, cancer stem cells, or neural stem cells.

In yet another aspect, a method of generating induced stem cells is described herein. The method includes contacting a population of non-stem cells with the composition of contained the induced exosomes, whereby induced stem cells are generated. In some embodiments, the composition is cell-free.

In some embodiments, the contacting step is performed by administering the composition to a subject in need thereof. The composition can be administered to the subject systemically or locally to a site in need thereof. The composition can contain exosomes released from stems cells obtained from the subject or another subject.

In some embodiments, the subject has a degenerative disease, tissue or organ damage, or cell defect. For example, the subject can have brain and spinal cord trauma, stroke, learning disabilities, Alzheimer's disease, Parkinson's disease, myocardial infarction, muscular dystrophy, baldness, deafness, vision loss, diabetes, or wound.

DETAILED DESCRIPTION

Figure 1:
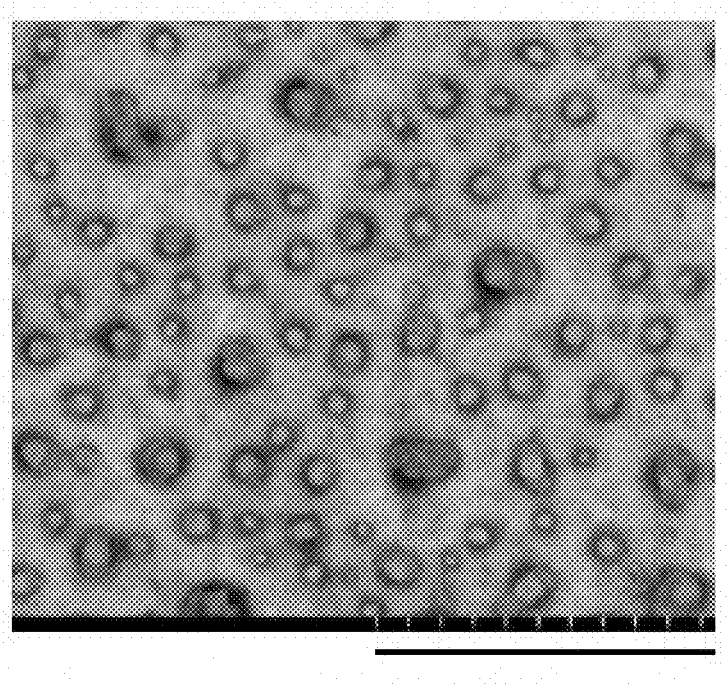
FIG. 1 includes a TEM image and a graph. (A) is a TEM image of the P4 medium fraction of NAMECs treated with GW627368X (GW) for 4 days. Scale bar, 1 µm. (B) is a graph showing the number of particles in the CM-P4 fractions of NAMEC culture counted by using NanoSight Nanoparticle Tracking analysis. Top panel: Quantification of exosome release is shown as the ratio of [P4 GAPDH marker level]/[cell number]. Data are means±SEM (n=3). *P≤0.05. **P≤0.005. Bottom table: Quantification of exosome release is shown as the number of particles of the CM-P4 fractions released per cell measured by nanoparticle tracking analysis.
Figure 1:
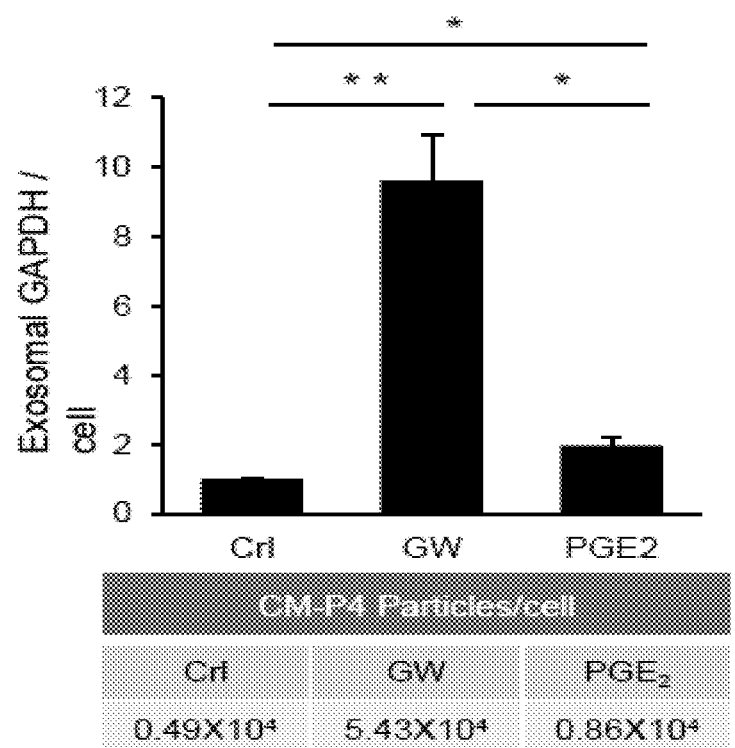

This disclosure describes a method of producing exosomes by culturing isolated stem cells with an effective amount of a prostaglandin E receptor 4 (EP4) antagonist to induce release of exosomes from the stem cells. The thus-produced exosomes are enriched for proteins and miRNAs required for maintaining stem cell homeostasis. Therefore, the exosomes produced by the method carry stem cell properties and can be used as an alternative to stem cell therapy.

As used herein, the term "non-stem cell" refers to a terminal-differentiated biological cell that cannot further differentiate to a specific cell under natural conditions. In some situations, the non-stem cells can divide to produce more non-stem cells. The so called "induced stem cells" refers to a class of stem cells that can be directly produced from mature non-stem cells via induction and exhibit differentiation ability of stem cells. For instance, the EP4 antagonist-induced exosomes are able to convert non-stem mammary epithelial cells into mammary stem cells, which are able to form mammary glands in vivo.

Any stem cells with differentiation potential can be used in the method for producing induced exosomes, including (but not limited to) embryonic stem cells, induced high-efficacy stem cells, cancer stem cells, and tissue stem cells. The tissue stem cells include, but are not limited to, mesenchymal stem cells, hematopoietic stem cells, mammary stem cells, neural stem cells, small intestinal stem cells, skin stem cells, umbilical cord blood stem cells, limbal stem cells, hair follicle stem cells, adipose tissue derived stem cells, bone marrow stem cells, corneal stem cells, and ovarian stem cells.

As used herein, the term "Prostaglandin E receptor 4 antagonist" or "EP4 antagonist" refers to (1) a molecule that inhibits the expression of Prostaglandin E receptor 4, such as an siRNA molecule or shRNA molecule; or (2) a molecule that inhibits the interaction between EP4 and its ligand PGE2 or a function of the interaction, including (but not limited to) PGE2 neutralizing antibodies, inhibitors blocking the production of COX-2 by PGE2, and inhibitors blocking the production of mPGES-1 inhibitors by PGE2.

EP4 antagonists include, but are not limited to, EP4 siRNA molecules, GW627368X, AH23848, L-161,982, CJ-023,423, ONO AE3 208, BGC 20-1531, MF498, and CJ-42794.

The stem cells can be cultured with an effective amount of the EP4 antagonist for 4-8 days, depending on the type of the stem cells and the amount of the EP4 antagonist. For example, an effective amount of an EP4 antagonist can be 1.0-40 (e.g., 1, 2, 5, 10, 15, 20, 25, 30, 35, or 40) μg/ml. In some embodiments, the method includes culturing mammary stem cells in a medium containing 1.0-10 μg/ml of the EP4 antagonist GW627368X for 4 days to induce release of exosomes. In some embodiments, the method includes culturing mesenchymal stem cells in a medium containing 20 μg/ml of the EP4 antagonist GW627368X for 8 days. The culturing step can also include culturing neural stem cells in a medium containing 20-30 (e.g., 25) μg/ml of the EP4 antagonist GW627368X for 4 days to induce release of exosomes.

In one embodiment, mammary epithelial stem cells are cultured in Mammary Epithieal Basal Medium (250 ml MCDB-170, 250 ml DMEM-F12, 1.2 g sodium bicarbonate, 2.5 μg EGF, 0.25 mg hydrocortisone, 2.5 mg insulin, 35 mg BPE) with an EP4 antagonist (e.g., 1 μg/ml or GW627368X or 4 μg/ml of AH23848) for 4 days to induce release of the exosomes.

In another embodiment, mesenchymal stem cells, cultured in MSC Medium (500 ml low-glucose DMEM, 25 ml vesicle-depleted Bovine serum, GlutaMAX 1%), are treated with an EP4 antagonists (e.g., 10 μg/ml of GW627368X) for 8 days to induce release of the exosomes.

The culture containing the stem cells and release exosomes can be centrifuged sequentially at 300 g for about 5 min to remove dead cells, at 2,000 g for about 20 min to remove cell debris, at 10,000 g for about 30 min, and then finally at 110,000 g for about 60 min to separate the exosomes from the culture supernatant. The exosome pellet can be washed in, e.g., PBS. The washed pellet can then be resuspended in PBS or other suitable medium or excipient.

The induced exosomes can have a diameter of 50 nm to 150 nm. As compared to exosomes released by stem cells not treated with an EP4 antagonist, the induced exosomes contain higher amounts of certain molecules, e.g., proteins and RNAs, that are associated with maintaining stem cell properties. For example, as compared to exosomes released by non-treated stem cells, the induced exosomes contain higher levels of one or more of CD44, CD90, integrin β1, integrin α6, CD81, GAPDH, N-cadherin, fibronection, CD146, CD91, cofilin, filamin A, CD91, CNP, talin, tropomyosin, galectin 3, Rap1, , β catenin, TGFβ-R1, TGFβ-R1, LRP6, Ago1, Ago2, FZD5, EGFR, HER2, Met, $EP_2$, PI3K, PDK1, Akt, p-Akt, c-Src, p-Src, SAPK/JNK, PSA, VCAM1, VEGFR2, VEGFR3, PDGFβ, NGFR, IL-2Rβ, IL-18Rβ, BMP-7, MIP-3a, RANTES, DR6, LIF, BDNF, TIMP1, VEGFa, and IL-10. The induced exosomes can also include higher levels of one or more of mir-17-92, mir-106a-363, mir-106b-25 clusters, mir-24, mir-130, mir-17, mir-18a, mir-20a, mir-20b, mir-24, mir-25, mir-29a, mir-106b, mir-130a, and mir-130b. The induced exosomes can also be enriched for lipid raft-associated proteins, e.g., CD44, CD90, Integrin β1, Integrin α6, EGFR, HER2, Met, LRP6, TGFβ-R1, TGFβ-R2, p-Akt, Akt, Ago1, and Ago2.

The induced exosomes can be used to induce stem cell formation in vitro and in vivo. For example, the exosomes can be administered to a subject to induce stem cell formation to treat various conditions such as degenerative diseases (e.g., brain and spinal cord trauma, stroke, learning disabilities, Alzheimer's disease, Parkinson's disease, myocardial infarction, and muscular dystrophy). The induced exosomes can also be used to promote cardiomyocyte formation, stimulate angiogenesis, or stimulate blood cell formation. Other used include treating baldness, deafness, vision loss, diabetes, orthopedic surgery and wound. The induced exosomes can be administered to a subject via any suitable route, e.g., topical or parenteral administration.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are herein incorporated by reference in their entirety.

Example 1. Production and Release of Induced Exosomes from Stem Cells by EP4 Antagonists Production and isolation of induced exosomes from basal/mesenchymal mammary epithelial stem cells (NAMECs).

Mouse NAMECs were isolated from 12-week-old virgin female C57BL/6 mice using procedures previously described by Mroue (Methods Mol Biol 2013; 945: 221-250). After culturing for 3 days, the cells were detached in accutase (eBioscience) for 20 min, and then neutralized with 5% FBS in PBS. Cell aggregates were further treated with Dispase (STEMCELL) for 20 min.

The isolated human mammary epithelial stem cells (NAMECs) were cultured in mammary epithelial cell basal medium (250 ml MCDB-170, 250 ml DMEM-F12, 1.2 g sodium bicarbonate, 2.5 µg EGF, 0.25 mg Hydrocortisone, 2.5 mg insulin, 35 mg BPE) with or without containing EP4 antagonist, i.e., GW627368X (GW) at 1 µg/ml, or AH23848 (AH) at 4 µg/ml, for 4 days. The culture medium was supplied with 0.5 µg/ml of GW or 2 µg/ml of AH23848 at the third day of the culturing period. For the induction of EP4 antagonist-induced exosomes from mouse mammary epithelial cells, cells were cultured in a medium containing 10 µg/ml of GW for 4 days.

The culture media were centrifuged at 300 g for 5 min to remove cells (P1), at 2,000 g for 20 min (P2), then at 10,000 g for 30 min (P3) all at 4° C. Dead cells and cell debris were removed at 300 g (P1) and 1200 g (P2). Finally, exosomes (P4) were separated from the supernatant by centrifugation at 110,000 g for 60 min. The P4 exosome pellet was washed once in PBS and then re-suspended in PBS for further application.

Production and Isolation of Induced Exosomes from Mesenchymal Stem Cells (MSCs).

Isolated MSCs were cultured in MSC medium (475 ml low glucose DMEM, 25 ml vesicle-depleted Bovine serum, 1% GlutaMAX) with or without an EP4 antagonist (GW at 20 µg/ml) for 8 days. The culture medium was supplied with 10 µg/ml of GW on the third day, and changed with fresh medium with newly prepared 20 µg/ml GW on the forth day, and supplied with 10 µg/ml of GW on the seventh day of the culturing period.

The culture media were centrifuged at 300 g for 5 min to remove dead cells (P1), at 2,000 g for 20 min (P2) to remove cell debris, then at 10,000 g for 30 min (P3) all at 4° C. Finally, exosomes (P4) were separated from the supernatant by centrifugation at 110,000 g for 60 min. The EV/exosome pellet was washed once in PBS and then re-suspended in PBS for further application.

Production and Isolation of Induced Exosomes from Neural Stem Cells (NSCs).

Isolated neural stem cells (NSCs) were cultured in NSC medium (225 ml low glucose DMEM, 225 ml F12, 50 ml vesicle-depleted Bovine serum) with or without an EP4 antagonist (GW at 20-30 µg/ml) for 4 days. The culture medium was supplied with 10-15 µg/ml of GW on the third day of the cultural period.

The culture media were centrifuged at 300 g for 5 min to remove dead cells (P1), at 2,000 g for 20 min (P2) to remove cell debris, then at 10,000 g for 30 min (P3) all at 4° C. Finally, exosomes (P4) were separated from the supernatant by centrifugation at 110,000 g for 60 min. The EV/exosome pellet was washed once in PBS and then re-suspended in PBS for further application.

The EM analysis of prepared exosome vesicles (P4) was performed as described previously by van Niel et al. (Gastroenterology 2001; 121:337-349). Briefly, exosomes purified as described above were fixed by 4% paraformaldehyde (PFA) in PBS and dropped on formvar/carbon-coated copper grids (Polysciences, Inc.). After washing, the samples were stained with 2% phosphotungstic acid and then viewed for transmission EM (TEM) using an electron microscope (HT7700, Hitachi).

As showed in FIG. 1, TEM analysis showed that the P4 medium (CM-P4) fraction of GW-treated NAMECs contained abundant membrane vesicles (FIG. 1, A). The particle numbers in the CM-P4 isolate were further analyzed using NanoSight Nanoparticle Tracking Analysis, showing that the EP4 antagonist significantly triggered the release of membrane vesicles as compared to the untreated NAMECs and PGE2 (1 µM)-treated NAMECs (FIG. 1, B).

Figure 2:
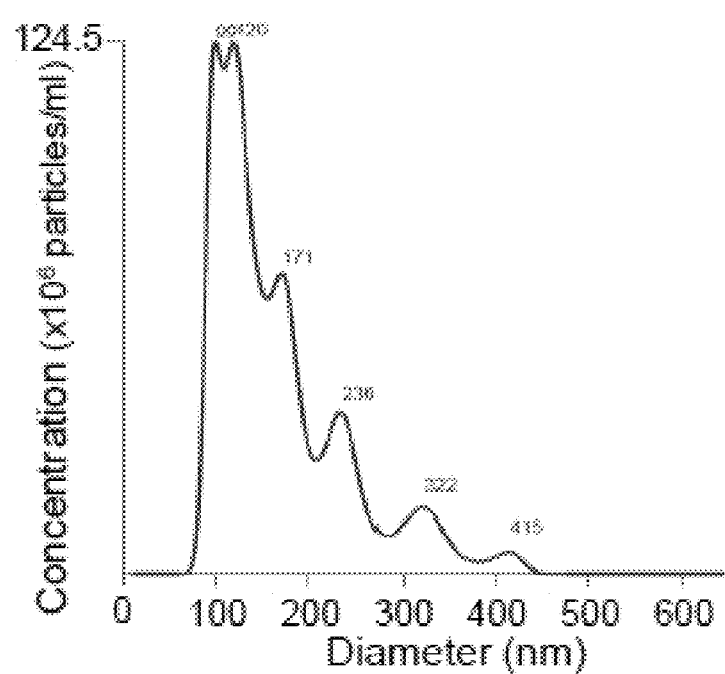
FIG. 2 includes graphs and blots showing analyses of GW-treated NAMEC P4 fractions. CM-P4 GW-treated NAMECs were collected and subjected to (A) NanoSight Nanoparticle Tracking Analysis (NTA) and (B) Dynamic Light Scattering/Zeta Potential Analysis (DLS). NTA shows the particle size and absolute particle concentration. DLS shows the particle size, mean diameter and relative particle number. D: particle diameter. RN: relative number. (C) is a blot showing the amounts of the CD44 stem cell marker and the CD81, CD9, TSG101, Alix, HSP70 and GAPDH exosome markers measured in the indicated CM-P4 fractions and cell lysates. The culture media and cell lysates were collected from the same number of NAMECs treated with vehicle (Crl), GW627368X (GW) or PGE2 (1 µM) for 4 days. (D) is a blot showing the amounts of the GAPDH and CD81 exosome markers and the CD44 stem cell marker measured in the CM-P4 fraction of NAMECs (CD44hi/CD24− stem cells) or CD44lo/CD24+ non-stem cells (HMLE cells) treated with vehicle (Crl) or GW for 2 days. 1×: P4 exosome fraction released by $1 \times 10^6$ cells; 2×: P4 exosome fraction released by $2 \times 10^6$ cells. The long exposure shows slight GAPDH signals in HMLE samples and no increase of the GAPDH signals in HMLE cells under GW treatment. (E) is a blot showing that the CD44 stem cell marker and GAPDH and CD81 exosome markers were measured in the indicated P4 conditioned medium fractions of NAMECs treated with vehicle (Crl), GW627368X (GW, 1 µg/ml), AH23848 (EP4 antagonist; 0.4, 2, 4 µg/ml), or AH6809 (EP1/2/3 antagonist; 0.8, 4, 8 µg/ml). (F) is a blot showing the HSP70, GAPDH and CD81 exosome markers measured in the indicated CM-P4 of NAMECs, NAMEC-shEP4-1 cells, and NAMEC-shEP4-2 cells treated with vehicle or with doxycycline (Dox, 2 µg/ml) (top panel). Doxyclycline (Dox) induced the production EP4 shRNA in NAMEC-shEP4 cells (bottom panel).
Figure 2:
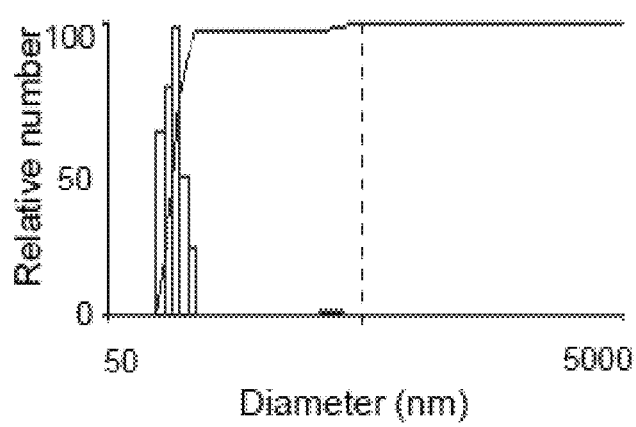
Figure 2:
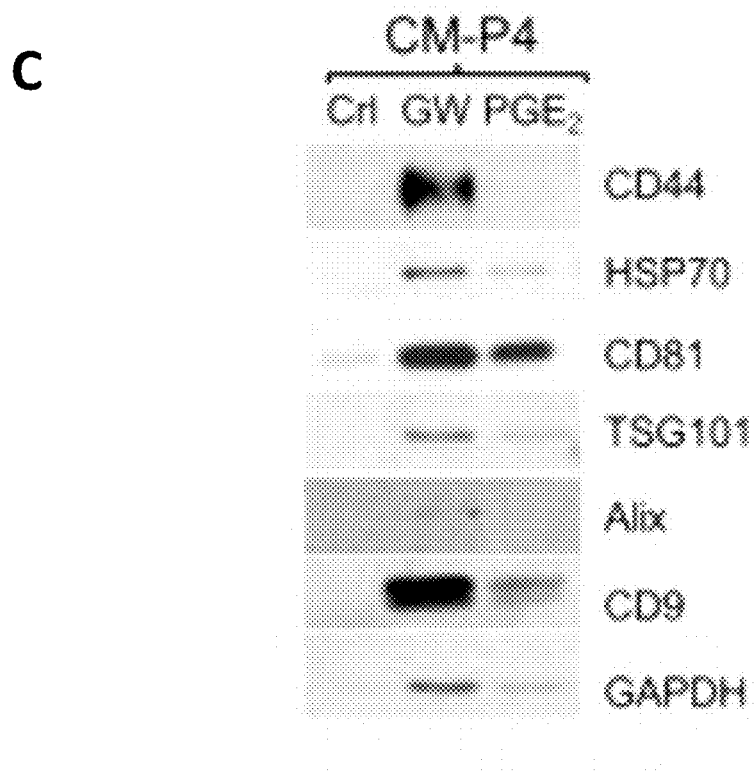
Figure 2:
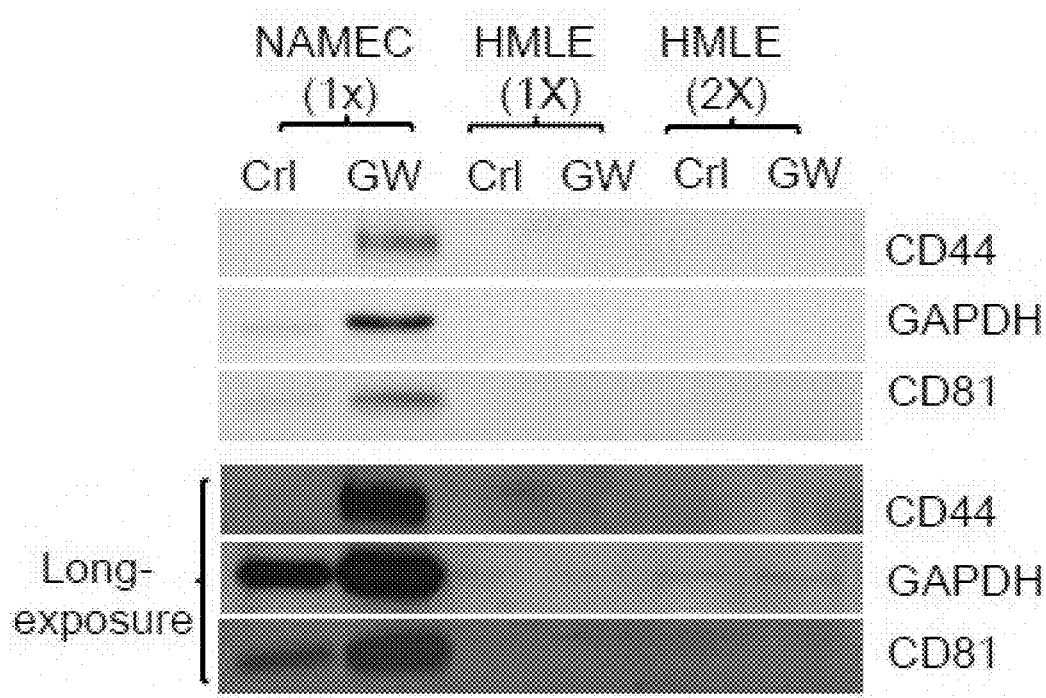
Figure 2:
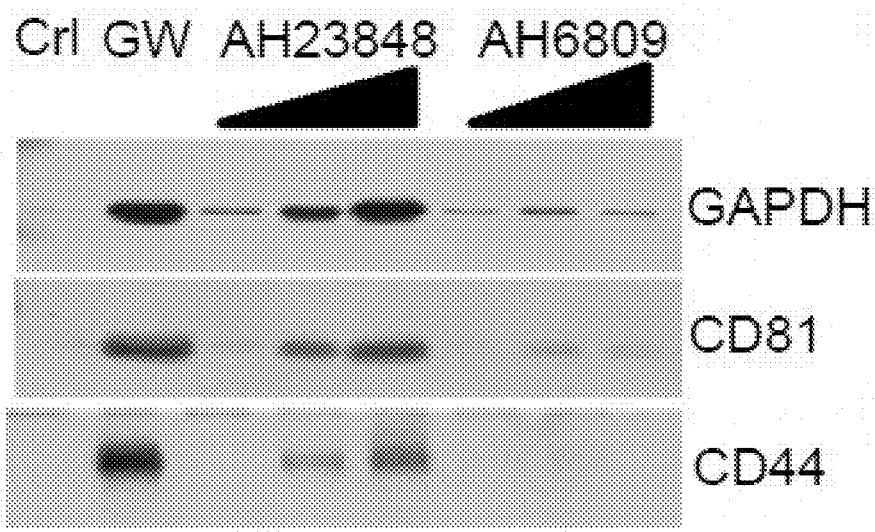
Figure 2:
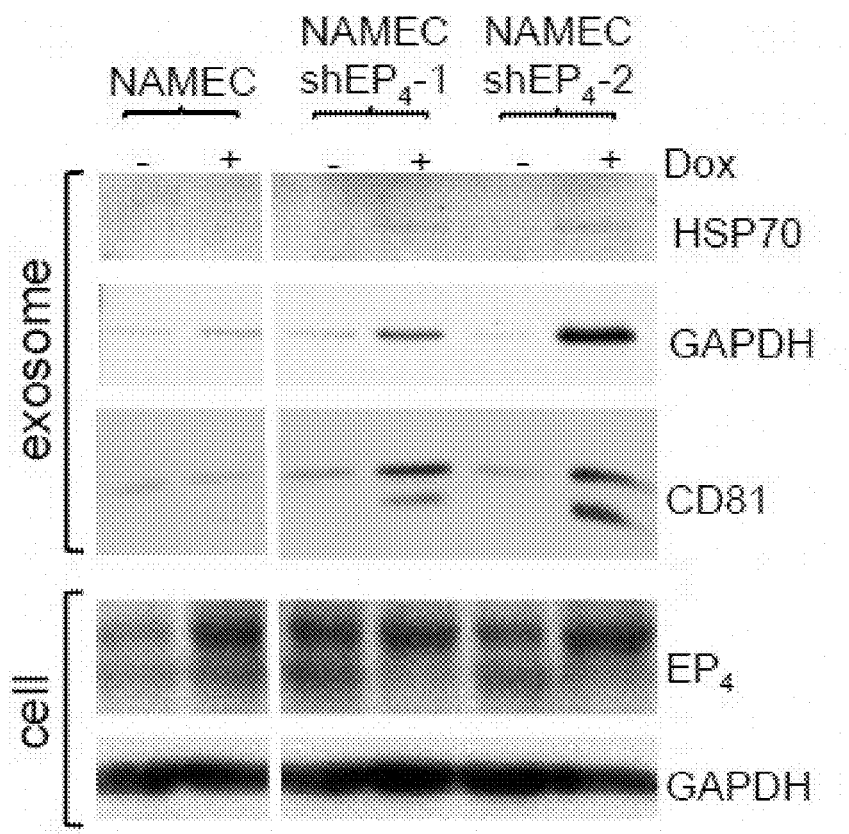

The result of NanoSight Nanoparticle Tracking Analysis (NTA) showed that the EP4 antagonist triggered the release of membrane vesicles ranging from 80-120 nm (concentration: $\sim 5.4 \times 10^4$ particle/cell; mean diameter: 97 nm. See, FIG. 1, B, and FIGS. 2, A and B. Untreated NAMECs and PGE2-treated NAMECs released many fewer and larger vesicles (concentration: $\sim 0.5 \times 10^4$ particle/cell; mean diameter: 173 nm and 201 nm). Large amounts of the general exosome markers CD81, CD9, TSG101, Alix, HSP70 and GAPDH were detected in the CM-P4 fractions of GW-treated NAMECs. See, FIG. 2, C. The results suggest that the release of these exosome markers occurs via the EP4 antagonist-induced exosomes.

As indicated by the exosome markers CD81, CD44 and GAPDH detected, the EP4 antagonist GW did not increase exosome release from non-stem mammary epithelial (HMLE) cells. GW EP4 antagonist induced substantial exosome release from basal mammary epithelial stem cells (MANECs), but not from their non-stem epithelial cell counterparts. See, FIG. 2, D. Exosome release from NAMECs was induced in a dose-dependent manner by AH23848, another EP4 antagonist, but was not significantly induced by AH6809, anEP1/EP2/EP3 antagonist. See, FIG. 2, E.

The effect of blocking EP4 signaling on exosome release was verified using shRNAs against EP4. NAMECs expressing the doxycycline (dox)-inducible EP4 shRNAs NAMEC-shEP4-1 and NAMEC-shEP4-2 were treated with doxycycline to knock down EP4 protein expression. Exosomes were released by dox-treated NAMEC-shEP4-1 and dox-treated NAMEC-shEP4-2 during the 96-h dox treatment, as demonstrated by the increased levels of GAPDH, CD81, and HSP70, exosomal markers in the CM-P4 fractions. See, FIG. 2, F.

Figure 3:
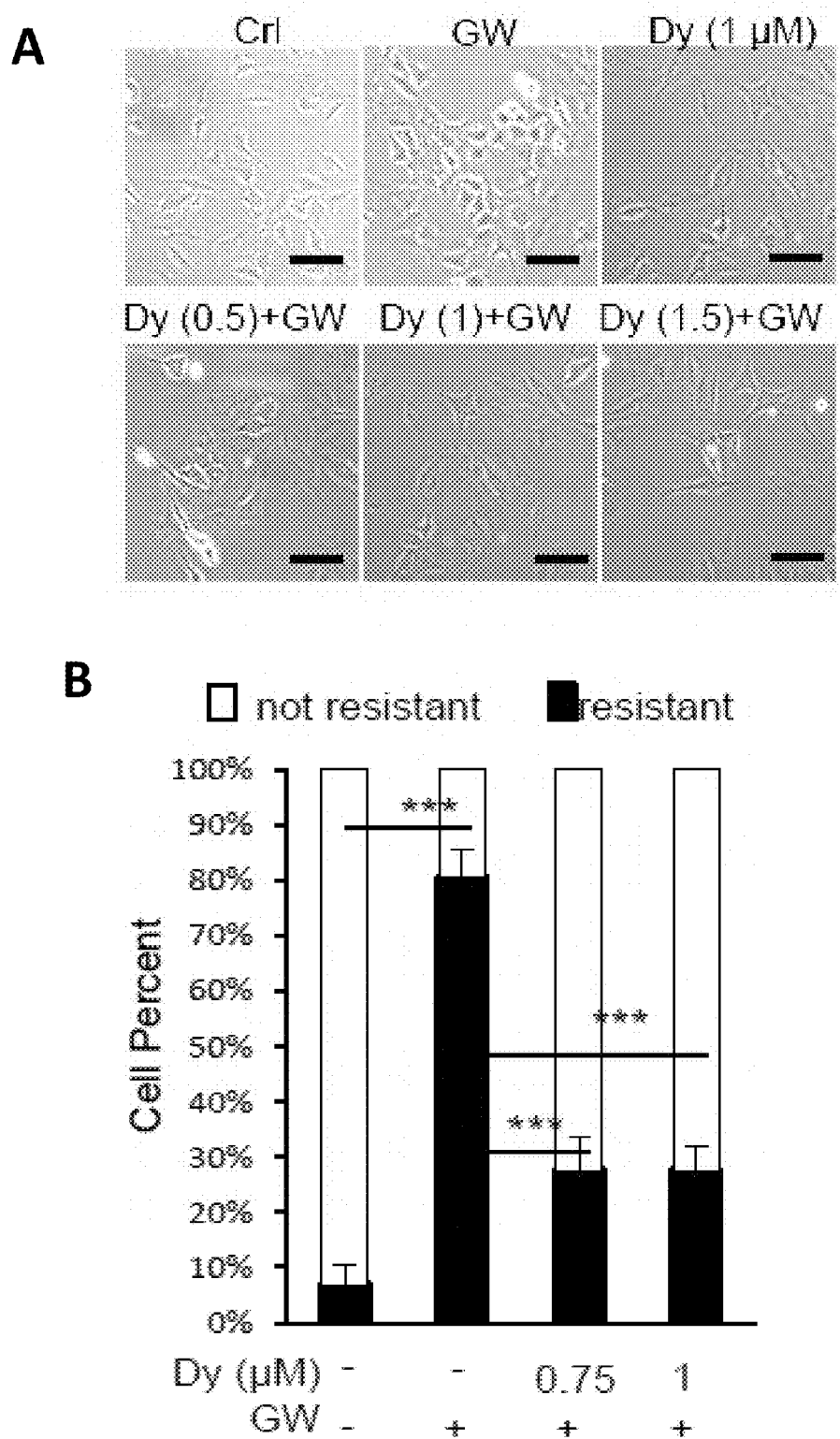
FIG. 3 includes a set of images and two graphs. (A) is a set of bright-field images of NAMECs treated with vehicle, GW627368X, Dynasore (1 µM), or GW627368X plus Dynasore (0.5, 1, 1.5 µM) for 4 days. Scale bar, 100 µm. (B) is a graph showing the percentage of NAMECs treated with vehicle, GW627368X, Dynasore (1 µM), or GW627368X plus Dynasore (0.75 and 1 µM) that were resistant to 0.05% trypsin. Data are means±SEM, (n=3). *P≤0.001. (C) is a graph showing Boyden chamber migration of NAMECs treated with vehicle (Crl), GW627368X, Dynasore (1 µM), or GW627368X plus Dynasore (0.5, 0.75, 1 µM) for 4 days. Data are means±SEM (n=3). P≤0.005. ***P≤0.001.
Figure 3:
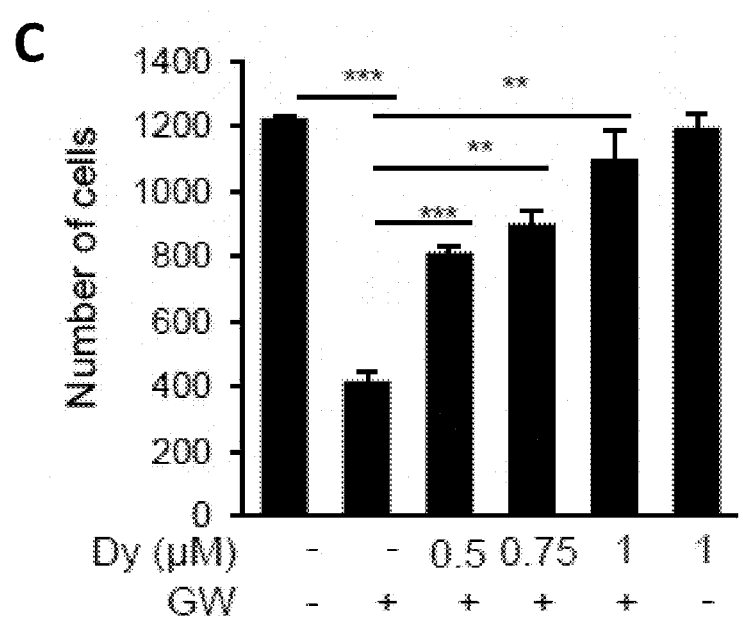

Blocking PGE2 signaling by either EP4 antagonists or EP4 shRNAs can induce exosome release from basal mammary epithelial stem cells. The mesenchymal NAMECs formed cobblestone-like, epithelial islands in the presence of GW (marked with colored dots). In contrast, NAMECs cultured in the absence of GW maintained their preexisting mesenchymal morphology (FIG. 3, A). The GW treated NAMECs that had undergone a complete mesenchymal-to-epithelial transition (MET) formed epithelial islands which became more resistant to disassociation by 0.05% trypsin treatment (FIG. 3, B). We concluded that blocking EP4 signaling induced a MET in NAMECs. In addition, the number of migrating cells was decreased ~60% by GW pre-treatment (FIG. 3, C), indicating that blocking EP4-mediated signaling caused a rapid loss of both mesenchymal morphology and migratory ability of basal mammary epithelial stem cells, which converted NAMECs to non-stem cells.

Example 2. Analysis of the Properties and Contents of EP4 Antagonist Induced Exosomes In this example, we further analyzed the contents of EP4 antagonist GW-induced and EP4 agonist PGE2-induced exosomes to find the differences between them which were responsible for their different abilities to transfer the stem cell state. As showed in FIG. 4, the amount of total exosomal proteins released by GW-treated NAMECs was much greater than that of NAMECs treated with vehicle (Crl) or with PGE2. In addition, the relative contents of various proteins in the GW-induced and PGE2-induced exosomes were also different.

Among these, GW-induced exosomes carried proteins essential to maintain mesenchymal/stem-like properties (e.g., N-cadherin, fibronectin, CD90, CD44, CD146, and CD91). In contrast, PGE2-induced exosomes carried the epithelial marker E-cadherin, which was not present in GW-induced exosomes. The results suggest that PGE2/EP4 signaling pathway modulates basal mammary epithelial stem cell morphology bidirectionally; the EP4 antagonist promotes MET by increasing the release of mesenchymal markers by exosomes and decreasing the release of E-cadherin by exosomes.

Proteins contributing to cell migration (e.g. integrin β1, integrin α6, cofilin, filamin A, CD91, CNP, talin, tropomyosin, gelectin 3, Rapt, and CD146), basal stem cell (SC) markers (e.g., CD44, CD90, integrin β1, and integrin α6), and β-catenin were also released from the GW-treated NAMECs via exosomes. The data suggest that the EP4 agonist induces exosomes release, which leads to loss of proteins important for maintaining stem-like properties and contributes to the changes in mesenchymal morphology, cell motility and stem cell identity of GW-treated basal mammary epithelial stem cells.

Figure 4:
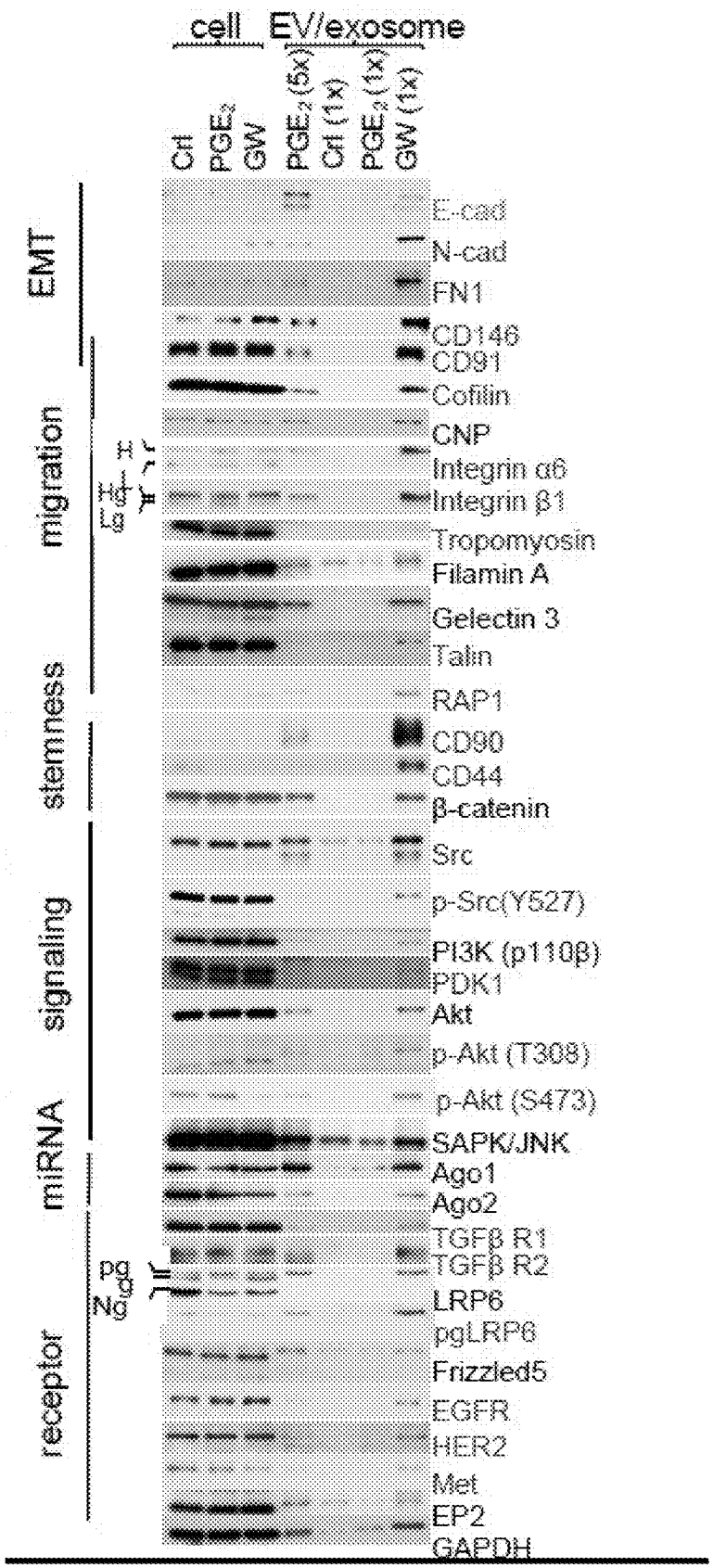
FIG. 4 shows proteins measured in the exosome fraction or in the cell lysate. The P4 exosome fractions and cell lysates were collected from NAMECs treated with vehicle (Crl), GW627368X (GW), or PGE2 for 4 days. 1×: P4 exosome fraction released by $2.5 \times 10^5$ cells; 5×: P4 exosome fraction released by $12.5 \times 10^5$ cells. Hg: Hg-integrin β1, Lg: Lg-integrin β1, H: H-integrin α6, L: L-integrin α6, pg: pg-LRP6, g: g-LRP6, Ng: Ng-LRP6.
Figure 5:
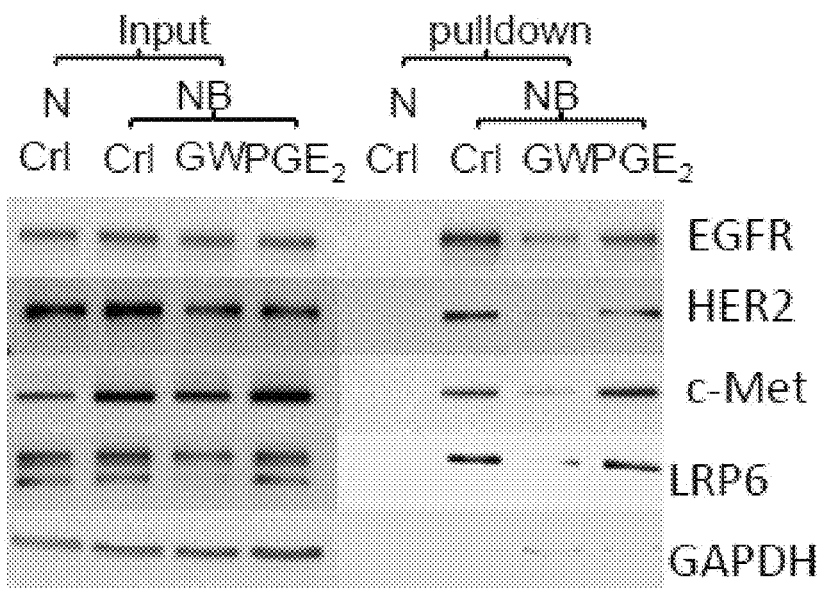
FIG. 5 shows the effects of EP4 antagonist on the distribution of cell surface receptors from NAMECs. (A) The surface proteins of NAMECs treated with vehicle (Crl), GW627368X (1 µg/ml), or PGE2 (1 µM) for 3 days were biotinylated and subjected to avidin pull-down. HER2, c-Met, LRP6, and EGFR proteins were measured by western blotting in the pull-down and input of whole cell lysates. N: control NAMECs. NB: biotinylated NAMECs. (B) Cell surface HER2, c-Met, LRP6, Frizzled-5, TGFβR1, TGFβR2, and EGFR in NAMECs treated with vehicle or in NAMECs treated with GW627368X (GW, 1 µg/ml) for 4 days were analyzed. Gray line: cells stained with specific primary antibody+Alexa 488-conjugated secondary antibody; Dark line: cells stained only with Alexa 488-conjugated secondary antibody as control.
Figure 5:
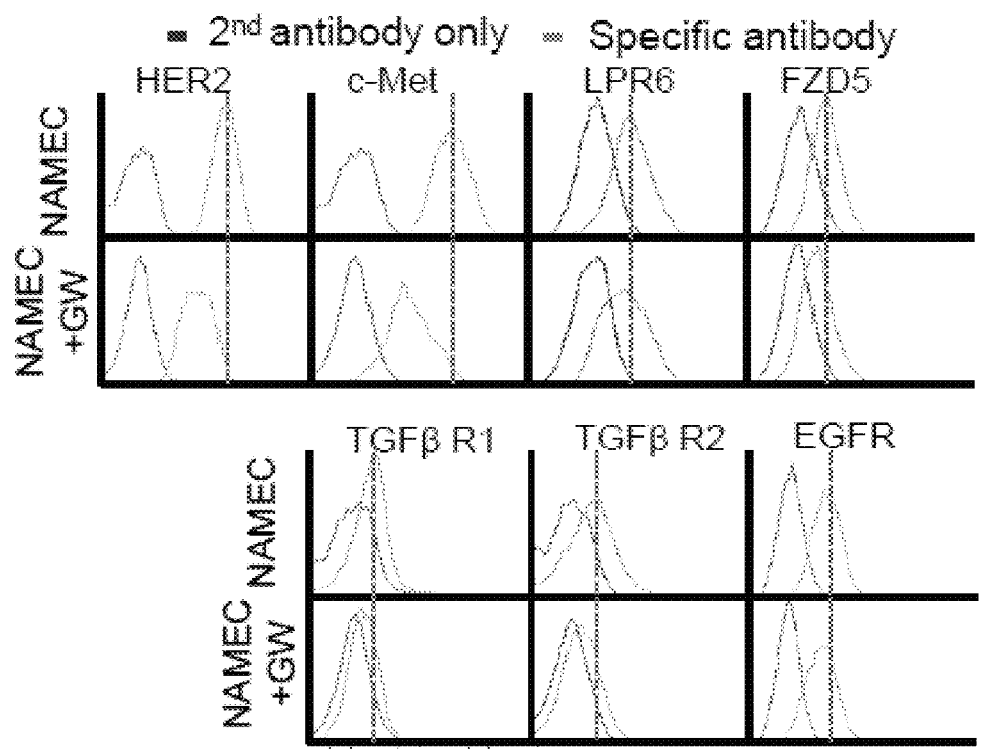

EP4 antagonist treatment of NAMECs induced the release of receptors and signaling proteins via exosomes. Signaling receptors (e.g., TGFβ-R1, TGFβ-R1, LRP6, FZD5, EGFR, HER2, Met and EP2) were detected in the GW-induced NAMEC exosomes (FIG. 4). In addition, the release of signaling receptors by blocking PGE2/EP4 signaling was reflected in the decreases of the cell-surface levels of these receptors in GW-treated NAMECs, measured by cell-surface protein biotinylation and by flow cytometry (FIGS. 5, A and B).

In addition, signaling proteins involved in PI3K signaling (PI3K, PDK1, Akt, p-Akt), canonical Wnt signaling (β-catenin), EGF signaling (c-Src, p-Src), and MAPK/non-canonical Wnt signaling (SAPK/JNK) were also released from NAMECs via GW-induced exosomes. By comparing the ratio of p-Akt-to-total Akt in the GW EP4 antagonist-treated cells and in the released exosomes, we found that p-Akt was preferentially recruited into the GW-induced exosomes relative to Akt (FIG. 4).

Figure 6:
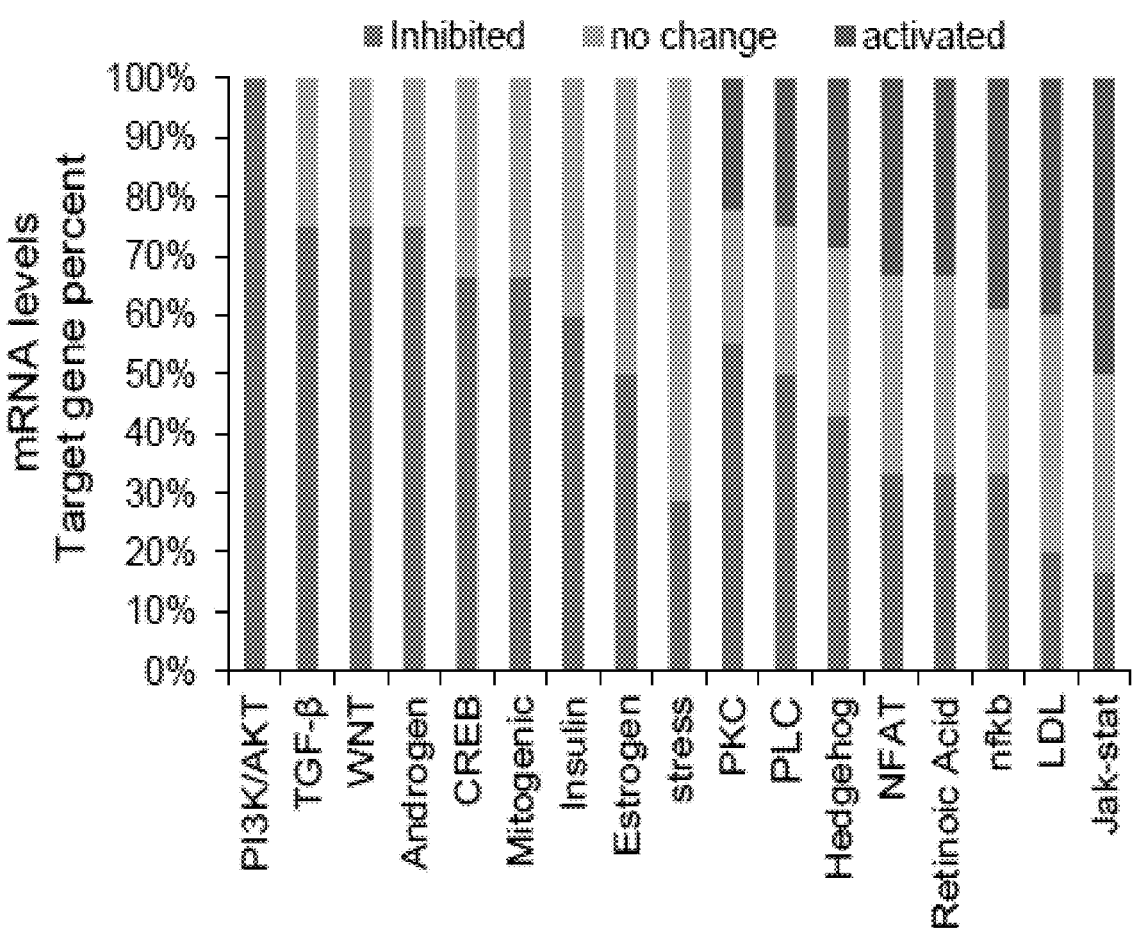
FIG. 6 shows an analysis of mRNA expression of the target genes of various signaling pathways in NAMECs and GW627368X-treated NAMECs (after 48-hour treatment) by PCR Arrays. The percentages of the target genes which, relative to NAMEC control cells, were inhibited, unchanged, or activated in GW627368X-treated NAMECs are presented in the plot.

To evaluate whether there is selective release of components of alternative signaling pathways, the activation and suppression of signaling pathways in GW-treated NAMECs were analyzed using RT2 Profiler PCR arrays. The results suggested that the pathways most inhibited by GW were the PI3K/Akt, TGF-β, Wnt and androgen pathways (FIG. 6). The decrease of p-Akt in GW-treated NAMECs and the enrichment of p-Akt in GW induced exosomes was reflected in inactivation of PI3K/Akt-signaling. Thus, EP4 antagonists are likely to interfere with the Akt-dependent signaling pathway by decreasing cellular p-Akt via exosome release.

In addition, the decreases of cell surface receptors EGFR, HER2, c-Met, TGFβ-R1, TGFβ-R1, LRP6 and FZD5 in GW-treated NAMECs, released in GW induced exosomes, were also reflected in inactivation of PI3K/Akt, TGF-β, and canonical/noncanonical Wnt signaling. These data suggest that blocking EP4 signaling can indirectly affect other cell-signaling pathways as a consequence of exosome release, by decreasing their surface receptors and/or signaling components, and then induce the transition of a mesenchymal/SC state of mammary epithelial stem cells to an epithelial state.

Figure 7:
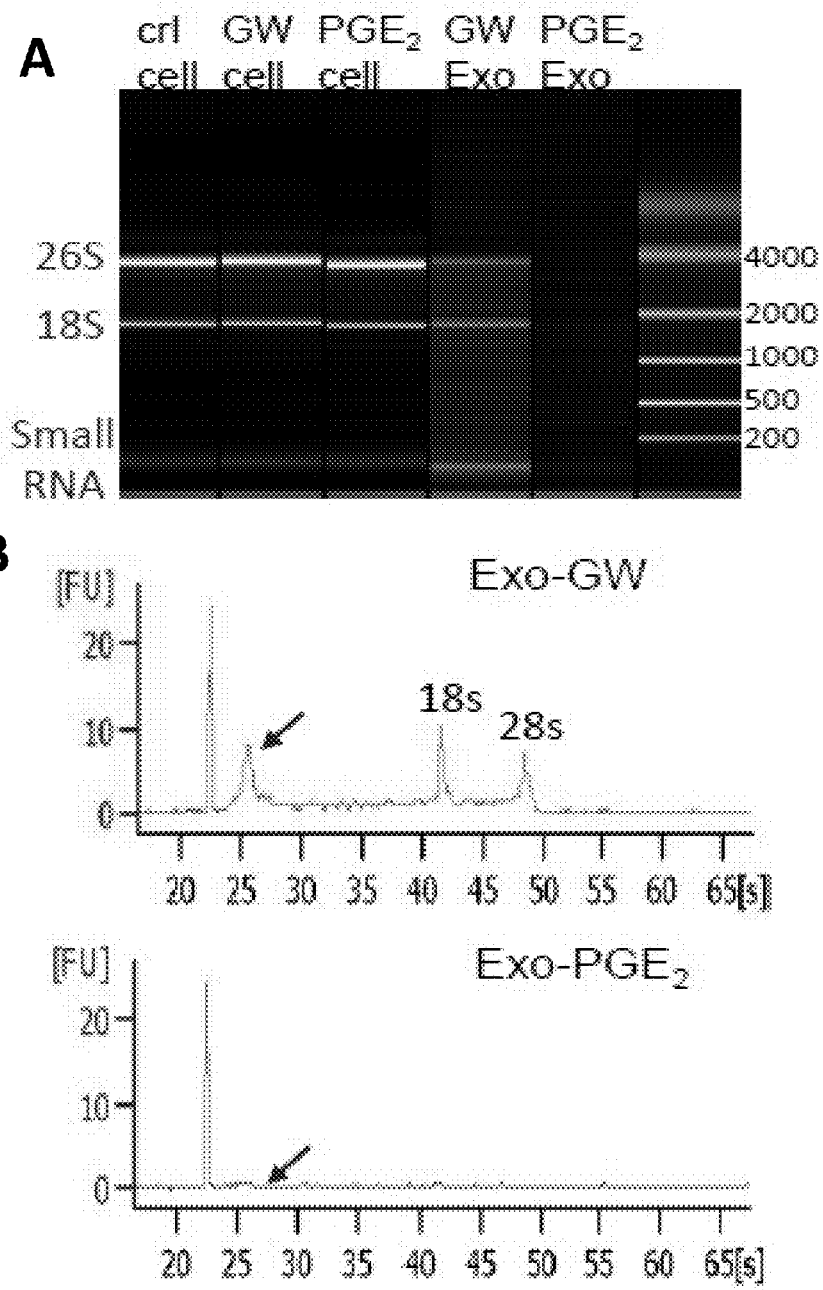
FIG. 7 shows an analysis of the RNAs of NAMECs and GW-induced and PGE2-induced NAMEC exosomes. (A) is an electrophoresis analysis of the RNAs. (B) is a set of electropherograms of the total RNAs from the same number of exosomes released by NAMECs treated with GW (Exo-GW) or PGE2 (Exo-PGE2) for 4 days, which were analyzed with the Agilent 2100 Bioanalyzer. Arrows: miRNA fractions.

In addition to SC markers, receptors, and signaling components, argonaute proteins (e.g. Ago1 and Ago2), essential catalytic components of the RNA-induced silencing complex (RISC), were also found in GW-induced exosomes, suggesting that the GW-induced exosomes may contain miRNAs. By comparing the ratio of miRNA-to-18S/26S RNA in NAMECs and in the GW-induced NAMEC exosomes, it was found that miRNAs were preferentially recruited into the GW-induced exosomes relative to total RNAs (FIG. 7, A). Furthermore, while the GW-induced exosomes contained abundant miRNAs, there was only a small amount of miRNAs detected in the PGE2-induced exosomes (FIG. 7, B).

Figure 8:
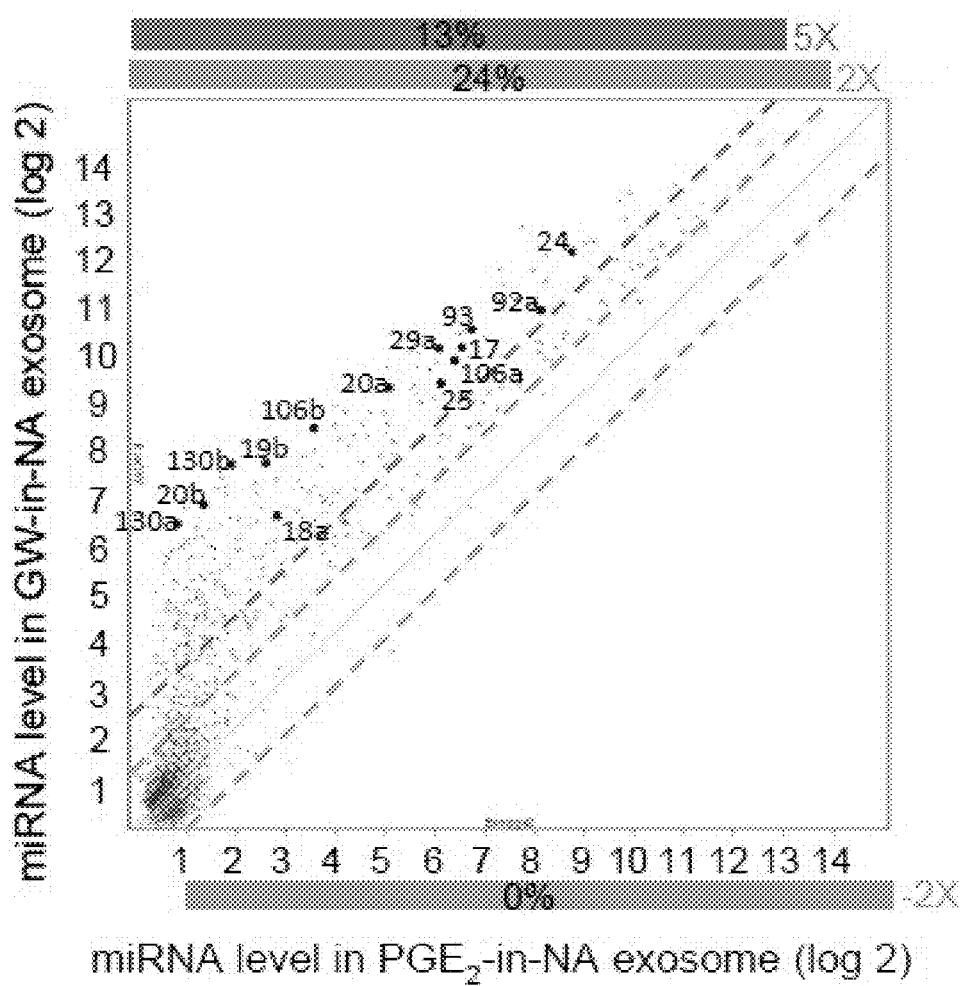
FIG. 8 shows the differential expression of miRNAs in the GW-induced exosomes, compared to that of PGE2-induced exosomes on a per-exosome basis, as determined by Affymetrix miRNA 3.0 arrays. Dark dashed line: 5-fold change cutoff. Lighter grey dashed line: 2-fold change cutoff. The miRNA levels were normalized using the exosomal GAPDH marker.

The miRNA content in the GW-induced and PGE2-induced exosomes was analyzed, on a per-exosome basis, using miRNA microarrays. Levels of 24% of the 1733 analyzed miRNAs were elevated (≥2 fold) in GW-induced exosomes, compared to that of PGE2-induced exosomes (FIG. 8). In contrast, there was no miRNA upregulated (≥2 fold) in PGE2-induced exosomes. The top 10 percent of up-regulated miRNAs (≥5 fold) in the GW-induced exosomes contained many miRNAs known to be involved in SC homeostasis and motility (e.g, mir-17-92, mir-106a-363, and mir-106b-25 clusters, mir-24, and mir-130). miRNAs involved in SC homeostasis, i.e. mir-17, mir-18a, mir-20a, it-20b, mir-24, mir-25, mir-29a, mir-106b, mir-130a, and mir-130b, were also highly enriched in the GW-induced exosomes when compared to the PGE2-induced exosomes. These data suggest that GW-induced exosomes, which carry miRNAs regulating SC homeostasis and motility, can mediate the alteration of stem cell properties.

It is known that proteins (such as CD44, CD90, integrins, EGFR, c-Met, HER2, LRP6, Akt, and TGFβR) can function differently when present in lipid raft (LRF) versus non-LRF. The LRF-associated forms of the proteins on plasma membranes usually actively mediate signaling. As showed in FIG. 4, NAMEC stem cells expressed different forms of integrin β1 (Hg-integrin β1 and Lg-integrin β1), integrin α6 (H-integrin α6 and L-integrin α6), and LRP6 (LRP6, pg-LRP6, g-LRP6 and Ng-LRP6). These different forms result from different states of phosphorylation and glycosylation. In NAMECs, Hg-integrin β1, H-integrin α6, and pg-LRP appeared in the LRF, while Lg-integrin β1, integrin α6, and Ng-LRP6 were only present in the non-LRF.

In the exosomal protein analysis (FIG. 4), we observed that, for the proteins which have distinct LRF-associated and non-LRF-associated forms (e.g. integrin β1, integrin α6, LRP6 and Akt/p-Akt), their LRF-associated forms (e.g. H-gintegrin β1, H-integrin α6, pg-LRP6 and p-Akt) were preferentially sorted into the GW-induced exosomes, as compared to their non-LRF-associated forms.

Figure 9:
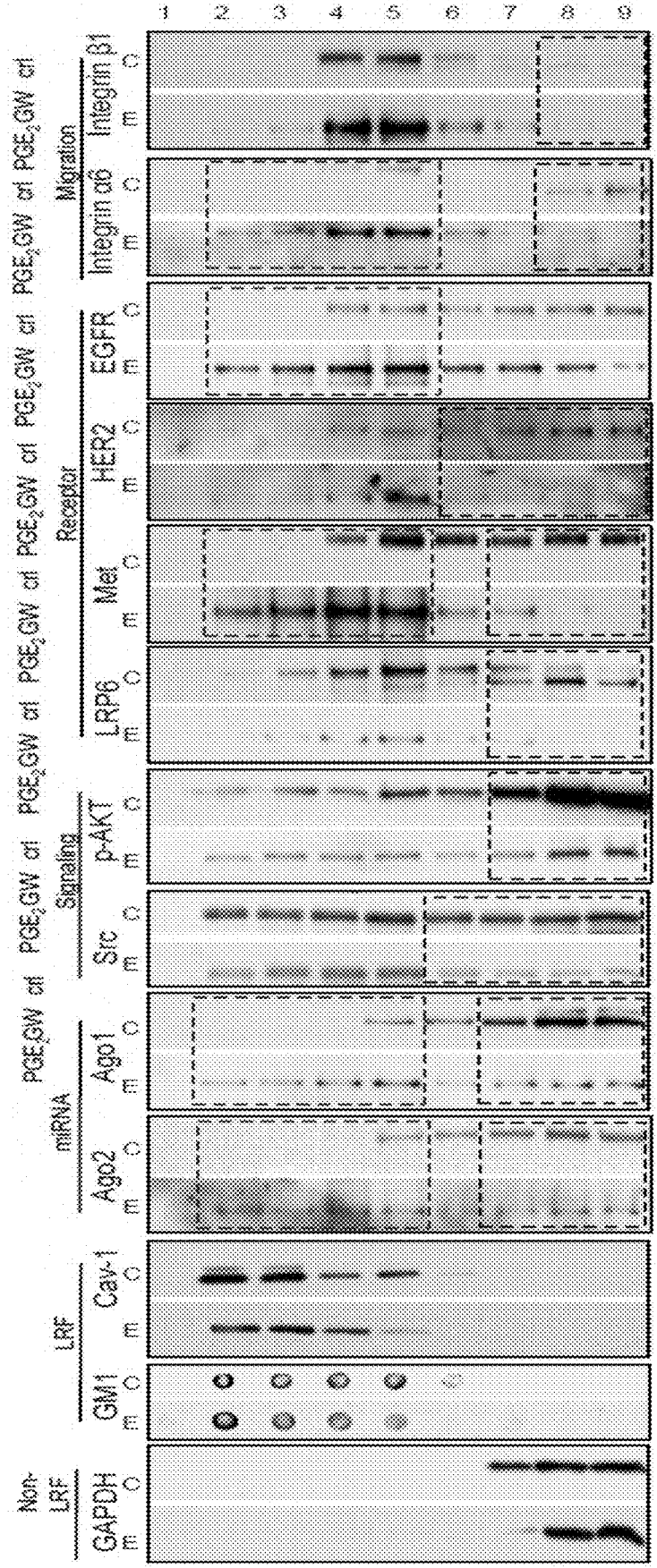
FIG. 9 is a set of Western blots showing proteins in lipid rafts. (A) shows a Western blot analysis of the indicated proteins in membrane fractions enriched in lipid rafts (LRF, fractions 2-5) or non-lipid rafts (non-LRF, fractions 7-9). The proteins were detected in the membrane fractions of GW-treated NAMECs and GW-in-NA exosomes by Western blotting along with ganglioside GM1 (dot blotting) and caveolin-1 (both markers of lipid rafts), and GAPDH (a marker of non-lipid rafts). C: cell. E: exosome. The right squares indicate the disappearance of protein from the non-LRF and the left squares indicate the appearance of protein in the LRF. (B) shows the proteins measured in the lipid rafts of GW- and PGE2-induced NAMEC exosomes. The proteins in the LRFs, fraction 2-5, of GW-in-NA and PGE2-in-NA exosomes were analyzed with Western blot. Lipid raft loading was quantified by GM1 and Cav-1 levels. (C) shows the indicated proteins measured in GW-induced exosomes released from NAMECs, siCav1 NAMECS, or siCav1+2 NAMECs. Loading control: exosomal GAPDH and β-actin. (D) shows the indicated proteins measured in GW-induced exosomes released from NAMECs treated with vehicle or MβCD. Loading control: exosomal GAPDH, β-actin, and CD81. (E) shows differential expression of miRNAs in the GWMβ-in-NA exosomes, compared to that of GW-in-NA exosomes on a per-exosome basis, as determined by Affymetrix miRNA 4.0 arrays. The miRNA levels were normalized using the exosomal GAPDH marker. (F) shows a Western blot analysis of TGFβR1, TGFβR2, p-Akt, Akt, and Ago2 in cell membrane fractions enriched in lipid rafts (LRF, fractions 2-5) or non-lipid rafts (non-LRF, fractions 7-9). NAMECs were treated with vehicle (Crl), GW627368X (1 μg/ml), or PGE2 (1 μM) for 4 days. Proteins were detected in these membrane fractions by western blotting along with ganglioside GM1 (dot blotting) and caveolin-1 as markers of lipid rafts, and with GAPDH as a marker of non-lipid rafts. The right square indicates the disappearance of protein from non-LRF of GW-treated NAMECs; the left squares indicate the appearance of protein in LRF of GW-treated NAMECs.
Figure 9:
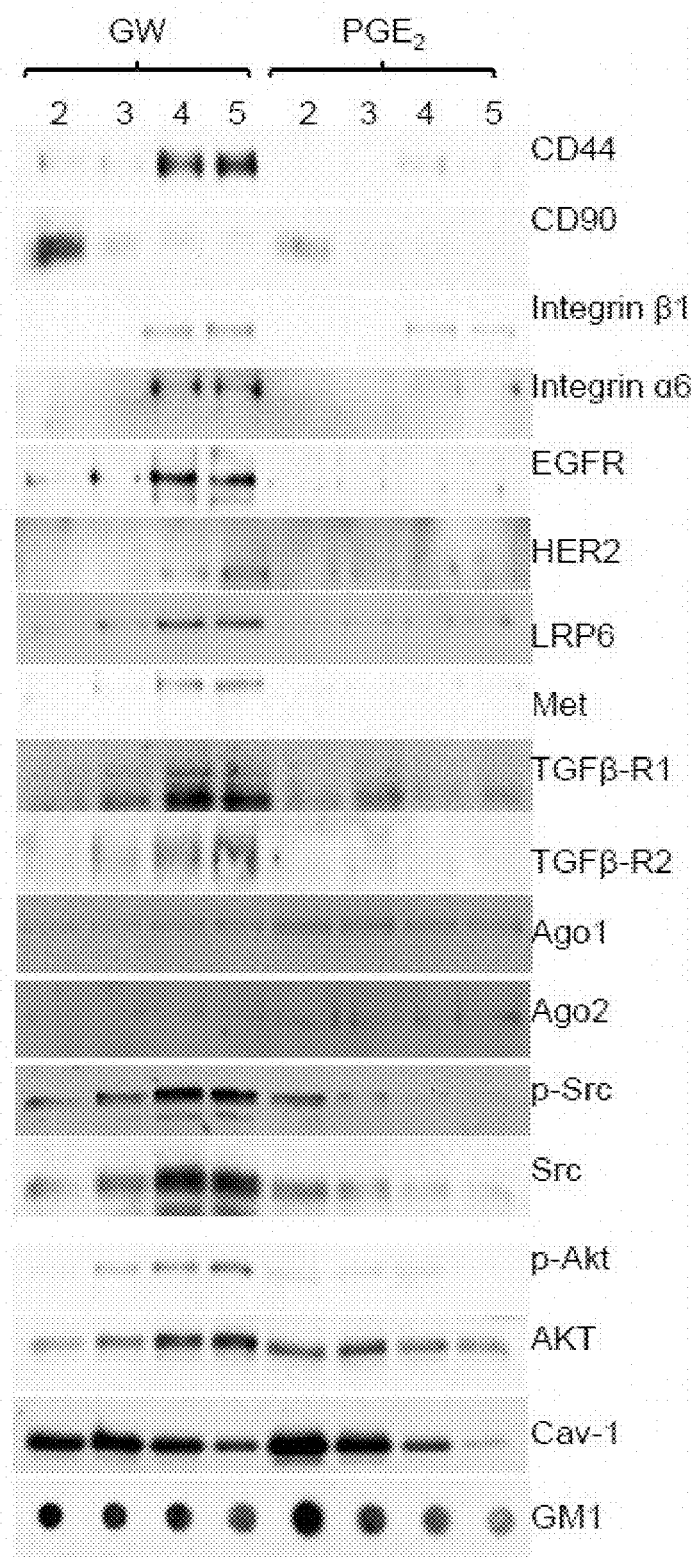
Figure 9:
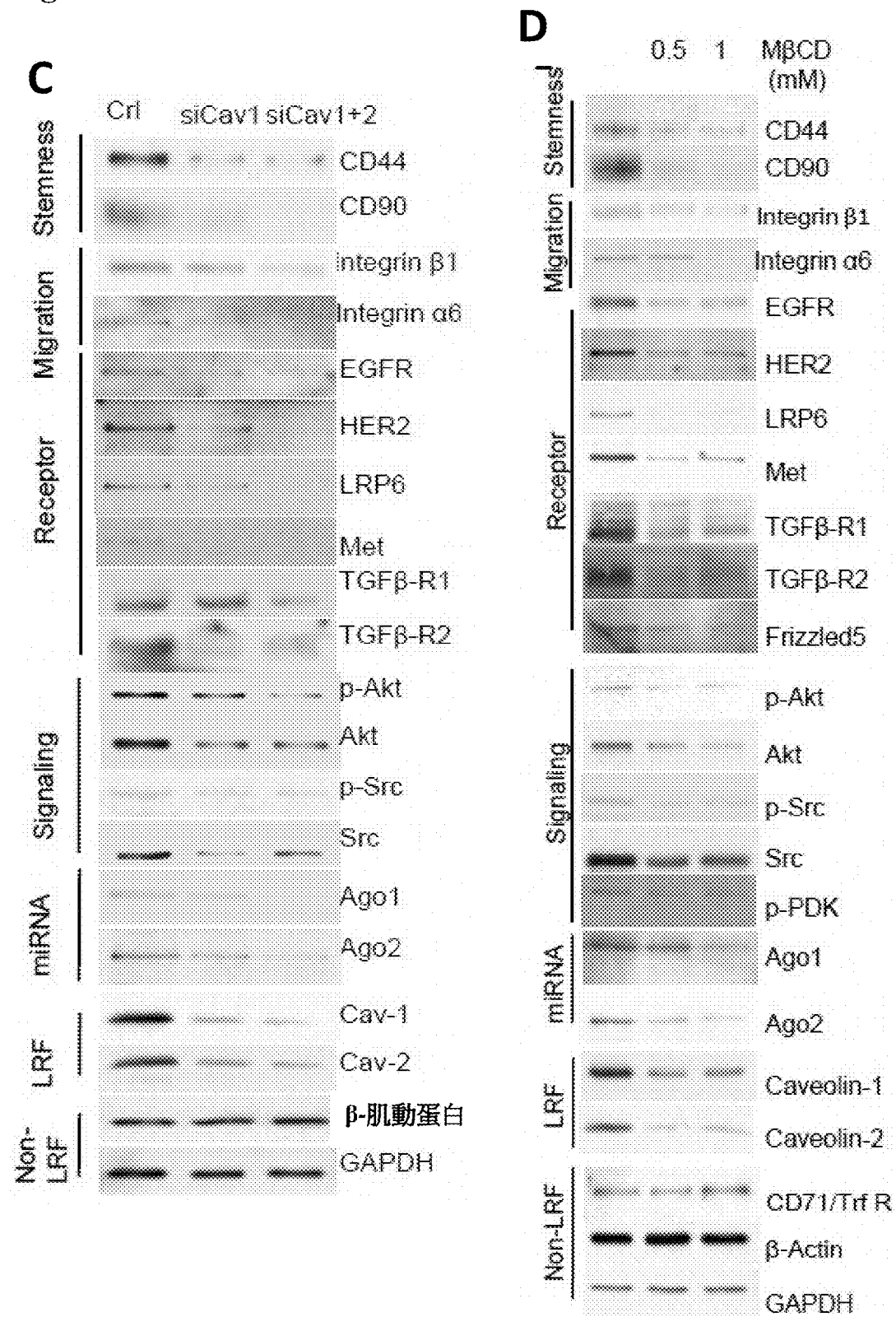
Figure 9:
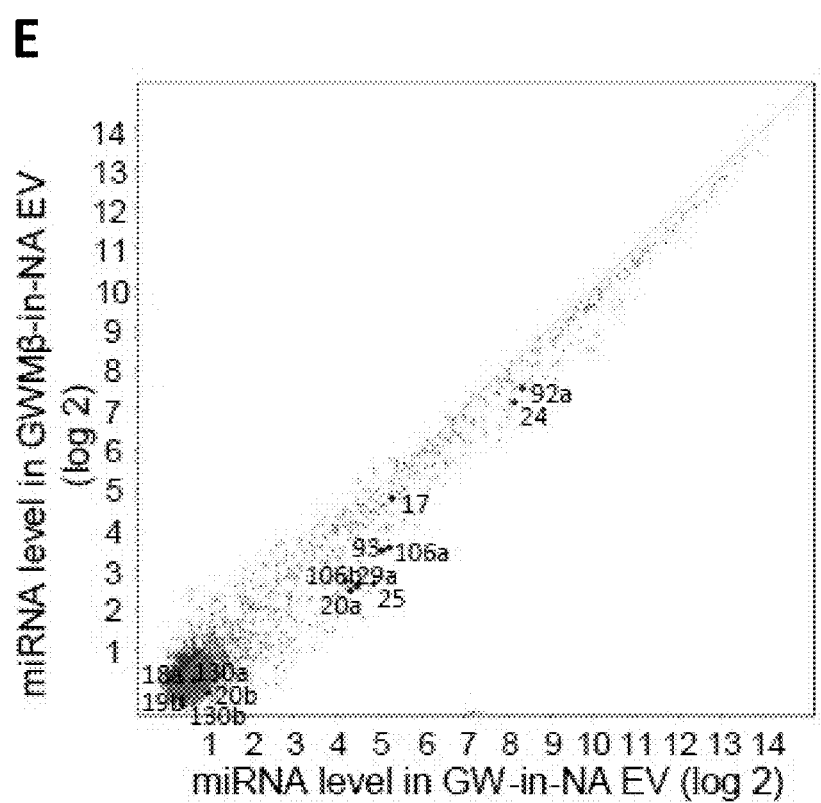
Figure 9:
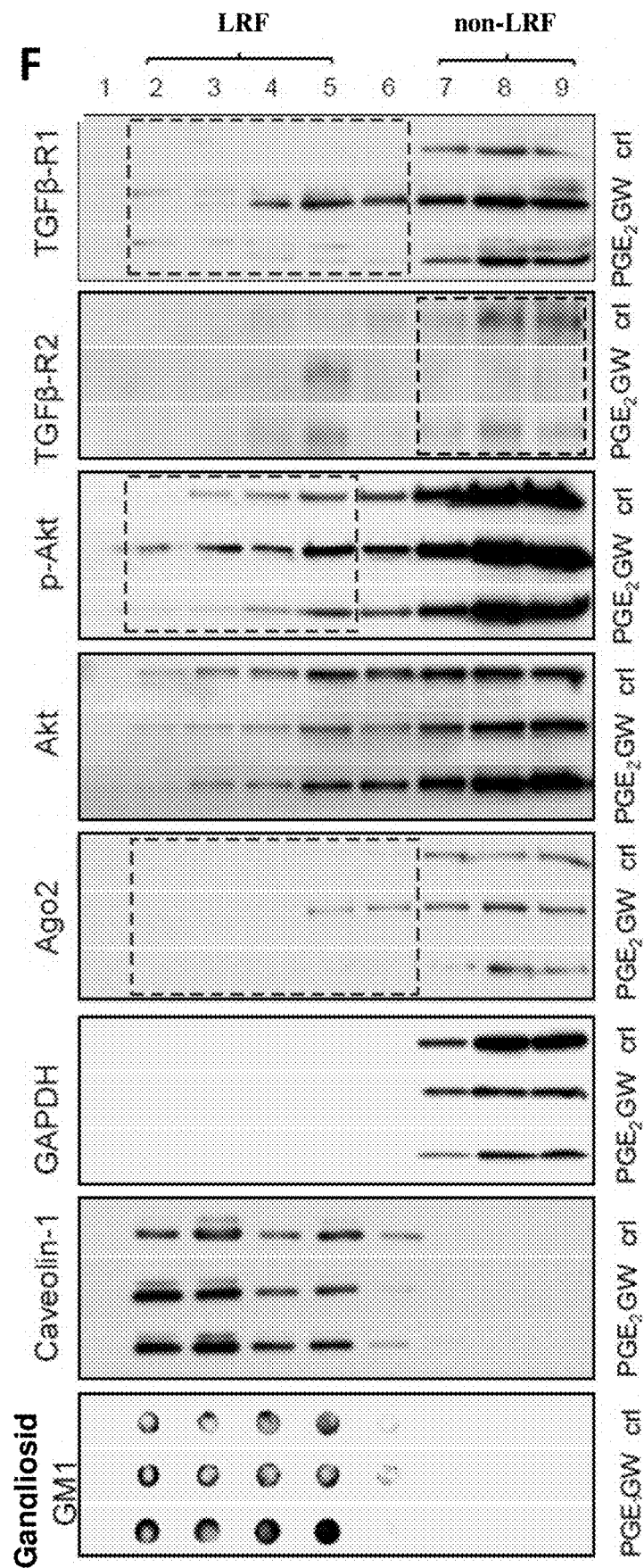

To verify whether the preferential sorting of LRF-associated forms of proteins into exosomes occurs for additional exosomal proteins, proteins isolated from the cellular and exosomal compartments of GW-treated NAMECs were further analyzed and compared using density gradient fractionation. By comparing the protein distribution between LRF and non-LRF in the cellular and exosomal compartments of GW-treated NAMECs, we observed that LRF-associated forms of the proteins (e.g., integrin β1, integrin α6, HER2, c-Met, EGFR, LRP6, p-Akt, Src, Ago1, and Ago2) were enriched in the exosomal compartments (FIG. 9, A). LRF-associated forms of many proteins were preferentially recruited into the GW-induced exosomes relative to non-LRF forms. Further analysis showed that, while the LRF of GW-induced exosomes carried abundant protein, the LRF of PGE2-induced exosomes contained little proteins (FIG. 9, B). The data suggested that the LRF appeared to be the determinant of exosomal protein differences between GW-induced and PGE2-induced exosomes.

Caveolae are morphologically identifiable LRF structures whose formation and maintenance depend heavily on the protein caveolin. The GW-induced exosomes released from caveolin knock-down NAMECs (siCav1 and siCav1+2) largely lost LRF-associated proteins (e.g., CD44, CD90, Integrin β1, Integrin α6, EGFR, HER2, Met, LRP6, TGFβ-R1, TGFβ-R2, p-Akt, Akt, Ago1, and Ago2), suggesting that caveolae contributed to protein sorting into GW-induced exosomes. See, FIG. 9, C.

Cholesterol is an important component of lipid rafts and depletion of cell membrane-associated cholesterol can disrupt lipid rafts. Lipid rafts of NAMAC were disrupted with methyl-β-cyclodextrin (MβCD). The amounts of proteins were measured and compared in GW-induced exosomes released from NAMECs treated with MβCD (GWMβ-in-NA exosomes) or without MβCD (GW-in-NA exosomes). Lipid raft-associated proteins largely decreased in GWMβ-in-NA exosomes because of disruption of cellular lipid rafts by cholesterol extraction; while levels of non-lipid raft membrane marker CD71/Trf R and cytosolic proteins (e.g. β-Actin, GAPDH) in exosomes were not altered by MβCD treatment. See, FIG. 9, D. The results suggested that cellular lipid rafts were required for the GW-elicited sorting of proteins into exosomes.

Disruption of cellular lipid rafts with MβCD also attenuated sorting of argonaute proteins, Ago1 and Ago2 into the EP4-antagonist-induced exosomes. Since argonaute proteins are essential catalytic components of the RISC complex, the decrease of argonaute proteins in the exosomes suggested that the exosomal miRNA content may also be affected by the disruption of cellular lipid rafts. Disrupting lipid rafts in NAMECs indeed altered small RNA in GW EP4 antagonist induced exosomes (FIG. 9, E). The miRNAs in GW-in-NA exosomes and GWMβ-in-NA exosomes were further analyzed and compared using miRNA array. Compared to GW-in-NA exosomes, 80% of the miRNAs were decreased in GWMβ-in-NA exosomes, including the SC homeostasis-related miRNAs enriched in GW-in-NA exosomes, e.g. mi-17, mir-18a, mir19b, mir-20a, mir-20b, mir-24, mir-25, mir-29a, mir-92a, mir-93, mir-106a, mir-106b, mir-130a, and mir-130b (FIG. 9, E). The data suggest that cellular lipid rafts are required for the GW-elicited miRNA sorting into exosomes.

Comparing protein distribution in lipid raft and non-raft fractions observed that EP4 antagonist triggered the shift of receptor proteins and signaling components from non-LRF into LRF fraction (FIG. 9, F), then being internalized with LRF. The data suggested that the endocytosis of the lipid rafts from cell membrane caused a decrease of the content of stem cell markers and signaling receptors in EP4-antagonist treated NAMECs.

Figure 19:
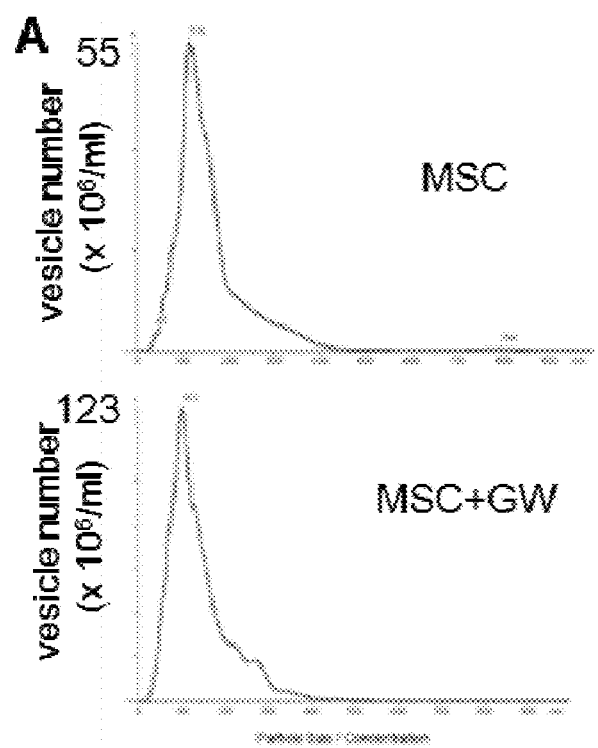
FIG. 19 shows that blocking EP4-mediated signaling with EP4 antagonists increased EV/exosome release from MSCs and increased protein and cytokine contents of the exosomes. (A) Vesicle number of GW-treated MSC P4 fractions was analyzed. CM-P4 GW-treated MSCs were collected and subjected to NanoSight Nanoparticle Tracking Analysis (NTA). (B) Proteins were measured in the EV/exosome fraction released by MSCs treated with vehicle DMSO, EP4 antagonists (GW), or EP4 agonist PGE2. The culture media were collected from MSCs treated with vehicle (DMSO), or GW for 8 days. EV/exosome proteins released by the same number of MSCs were loaded for Western blotting. (C) Cytokines were measured in the EV/exosome fraction released by MSCs treated with DMSO (MSC) or EP4 antagonist (MSCGW). Culture media were collected from MSCs treated with vehicle DMSO, or GW for 8 days. EV/exosome cytokines released by the same number of MSCs were measured using cytokine arrays (C) and Bioplex (D; IL-10). Proteins/cytokines increased in EVs released by GW-treated MSCs (MSCGW) are indicated in panel (C and D).
Figure 19:
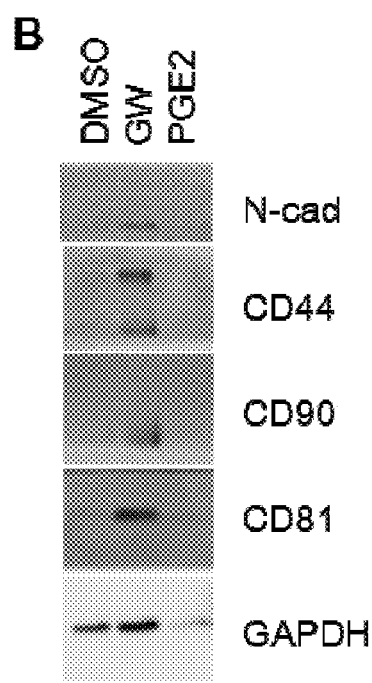
Figure 19:
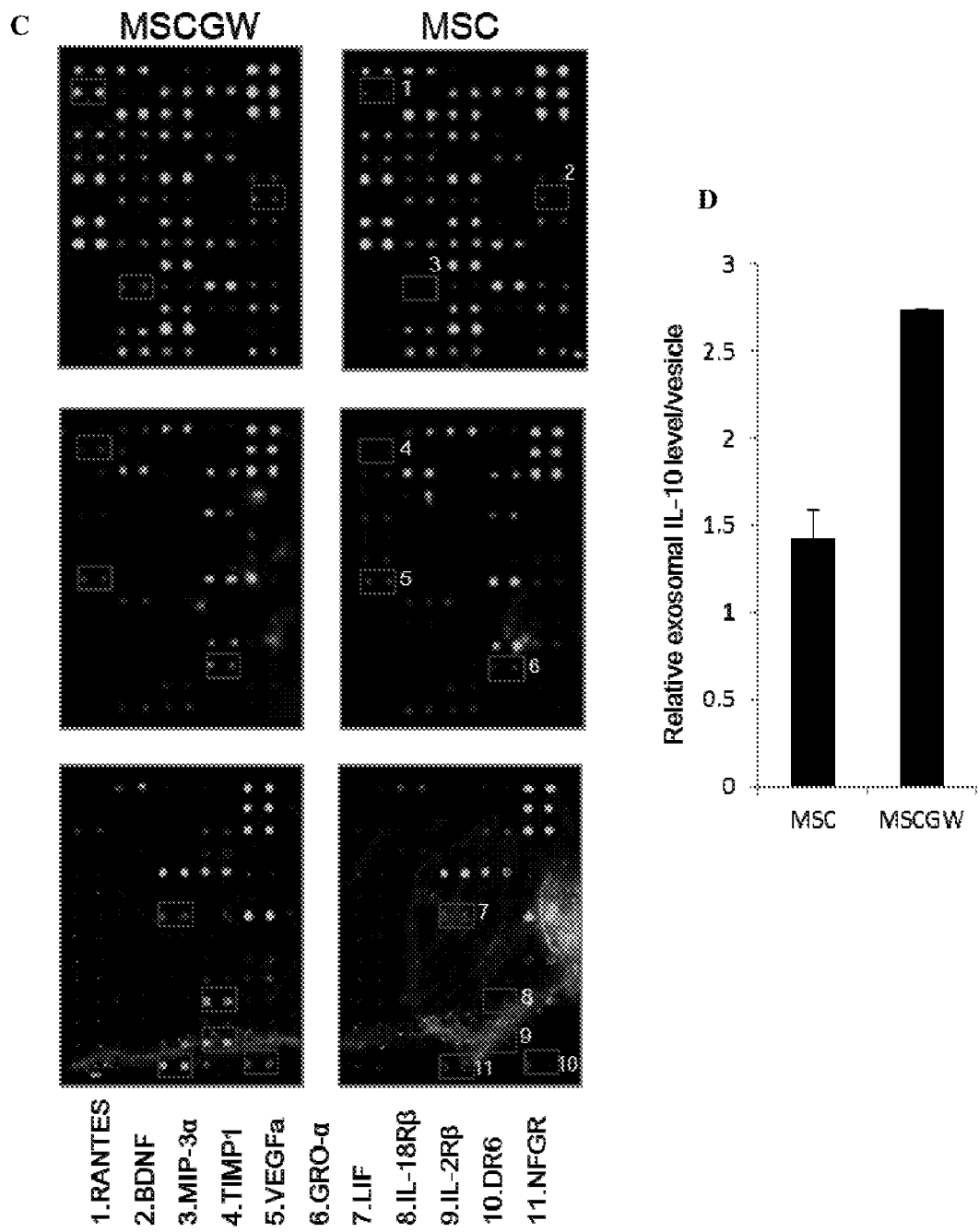

Similar results to NAMECs were obtained in GW-treated mesenchymal stem cells (MCSs). See FIGS. 10, A and B; and FIG. 19, A-D. Blocking EP4-mediated signaling with the EP4 antagonist increased the release of EVs/exosomes, and the level of essential proteins maintaining MSC properties in GW-induced exosomes, including cell surface MSC markers, cell surface receptors, signaling proteins and cytokines PSA, VCAM1, VEGFR2, VEGFR3, PDGFβ, NGFR, MPIF1, IL-2Rβ, IL-18Rβ, BMP-7, MIP-3α, RANTES DR6, LIF, BDNF, TIMP1, VEGFa, IL-10. See, FIG. 10, B; and FIG. 19, B-D.

Figure 11:
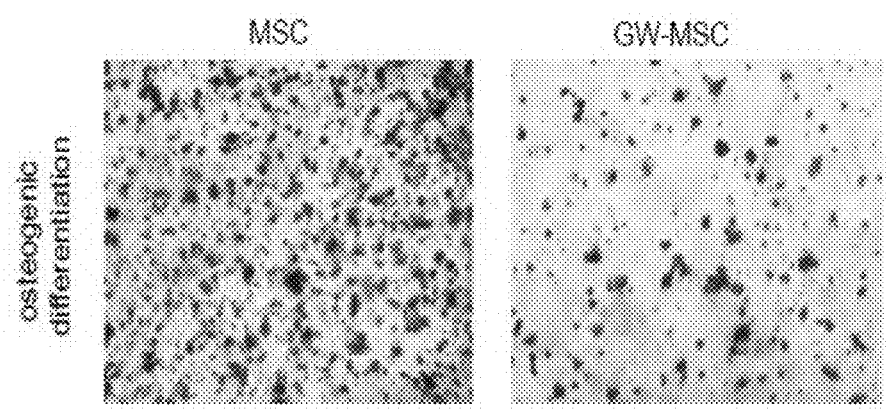
FIG. 11 shows a comparison between differentiation of MSCs and EP4 antagonist GW-treated MSCs. (A) and (B) show osteogenic differentiation of MSCs and EP4 antagonist GW-treated MSCs. MSCs were cultured in osteogenic differentiation medium and then stained with Alizarin Red S. Osteogenic differentiation was quantified by measuring the optical density (OD) of Alizarin Red S staining. (C) shows adipogenic differentiation of MSCs and EP4 antagonist GW-treated MSCs. MSCs were cultured in adipogenic differentiation medium. Cells were then stained with oil red O. (D) shows neural differentiation of MSCs and EP4 antagonist GW-treated MSCs. MSCs were cultured in neural differentiation medium for 7 or 14 days and then analyzed for the expression of neuronal marker tublin β3 and NeuN using western blotting.
Figure 11:
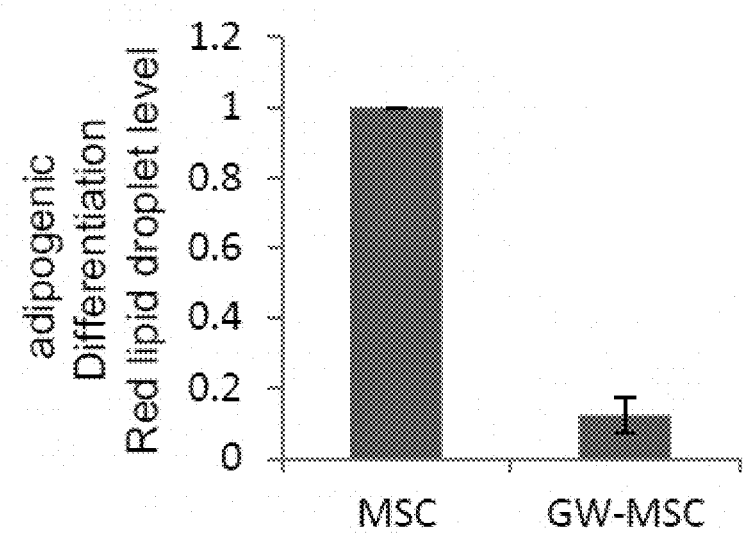
Figure 11:
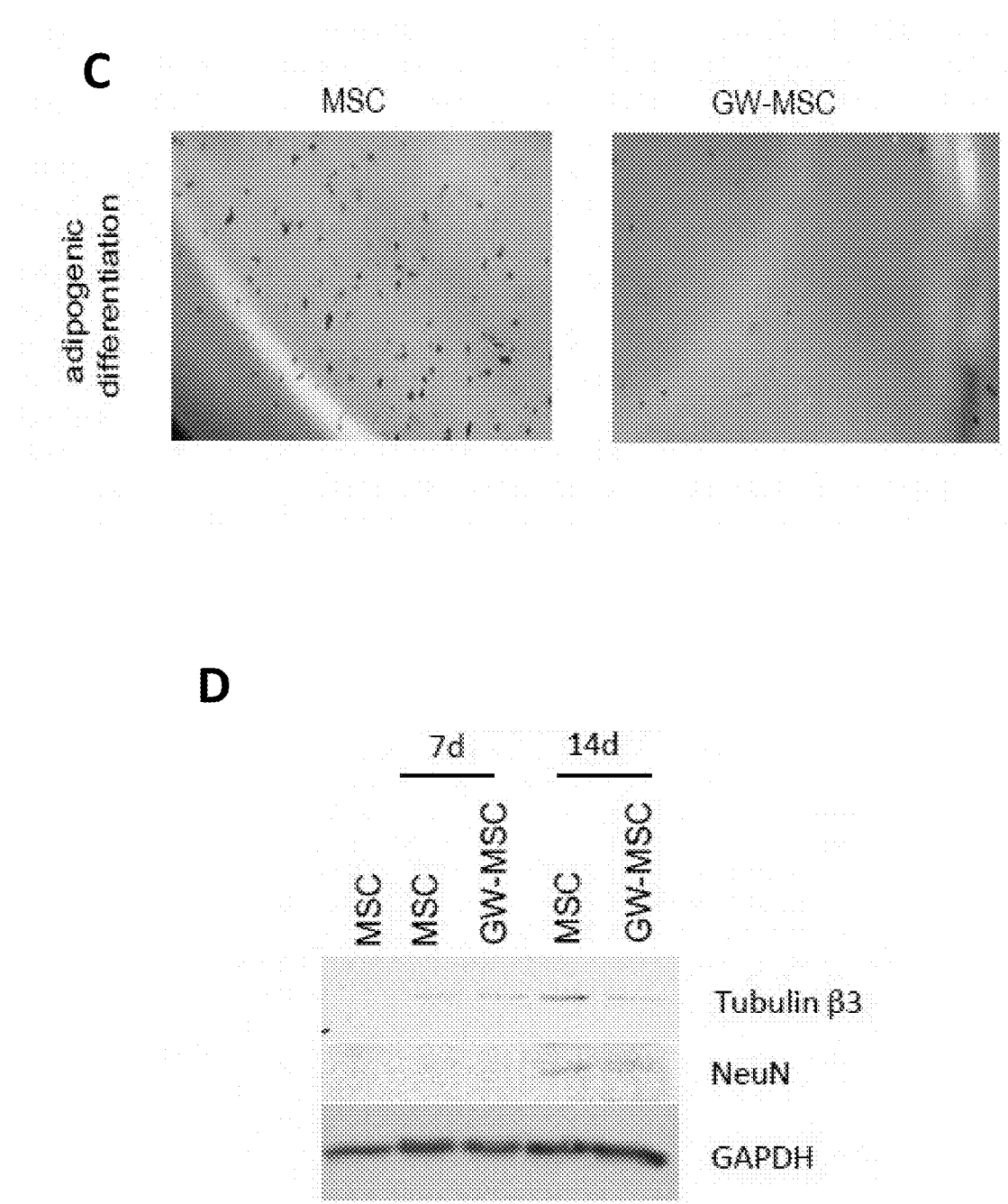

GW-treated MSCs were cultured in osteogenic differentiation medium, adipogenic differentiation medium and neuron differentiation medium, respectively. As showed in FIG. 11, the abilities to differentiate into osteoblasts, adipocytes or nerve cells were much lowered in GW-treated MSCs, as compared with non-treated MSCs (FIG. 11, A-D). The results suggested that GW-treated MSCs significantly lost their original stem cell properties.

Figure 10:
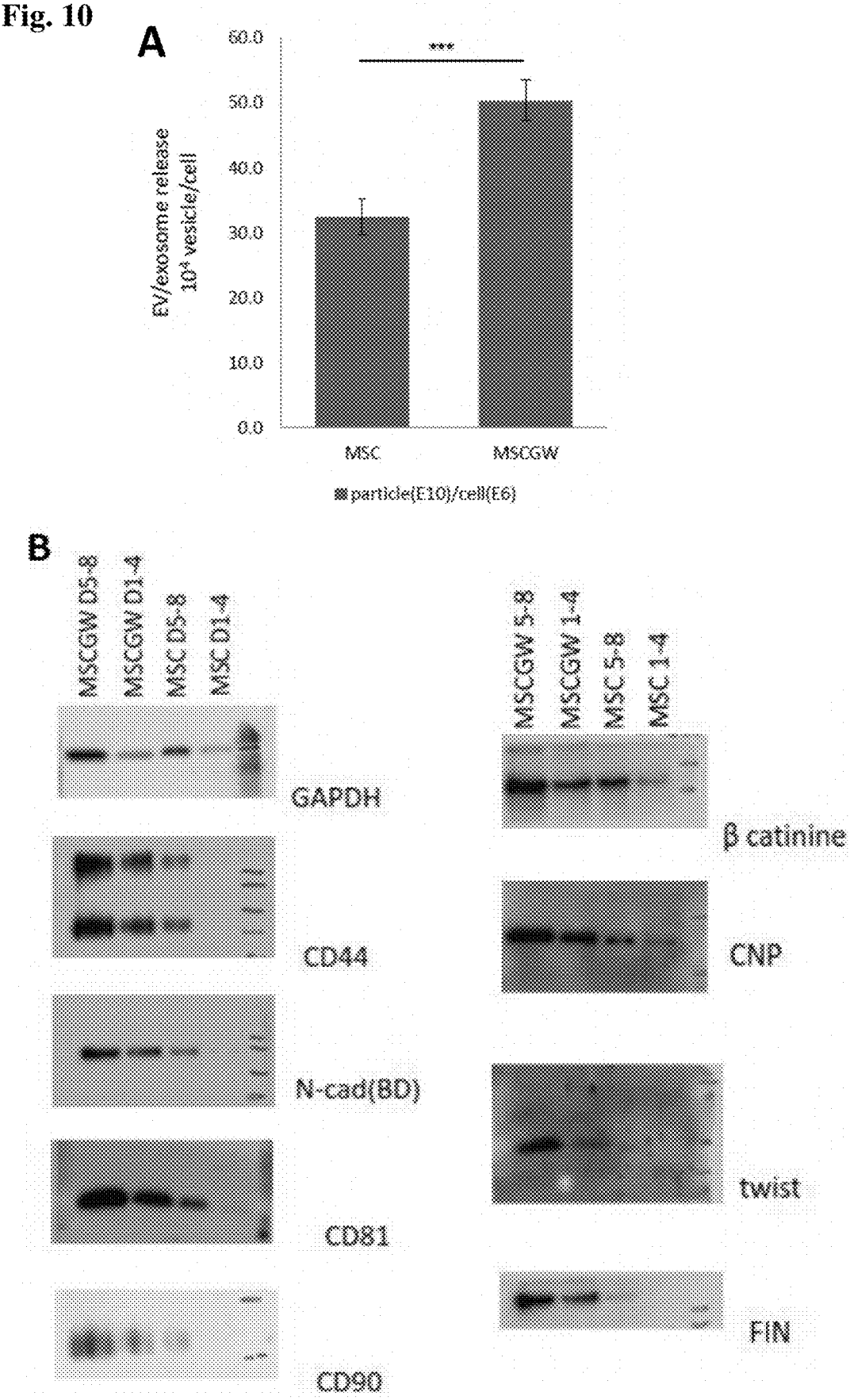
FIG. 10 includes blots and a graph. (A) is a graph showing vesicle number analysis of GW-treated mesenchymal stem cells (MSCs) P4 fractions. The CM-P4 GW-treated MSCs were collected and subjected to NanoSight Nanoparticle Tracking Analysis (NTA). Quantification of EV/exosome release is shown as the ratio of [vesicle number]/[cell number]. Data are means±SEM (n=3). ***P≤0.001. (B) is a set of blots showing the protein contents measured in the EV/exosome fraction released by MSCs treated with vehicle DMSO (MSC) or EP4 antagonists (MSCGW). The culture media (D1-4: conditioned medium from day 1 to day 4; D5-8: conditioned medium from day 5 to day 8) were collected from MSCs treated with vehicle (MSC), or GW (MSCGW) for 8 days. (C) is a set of blots showing the protein contents measured in the EV/exosome fraction released by neural stem cells (NSCs) treated with vehicle DMSO or EP4 antagonists. The culture media were collected from MSCs treated with DMSO or GW for 4 days. EV/exosome protein released by the same number of NSCs was loaded in the Western blotting.
Figure 10:
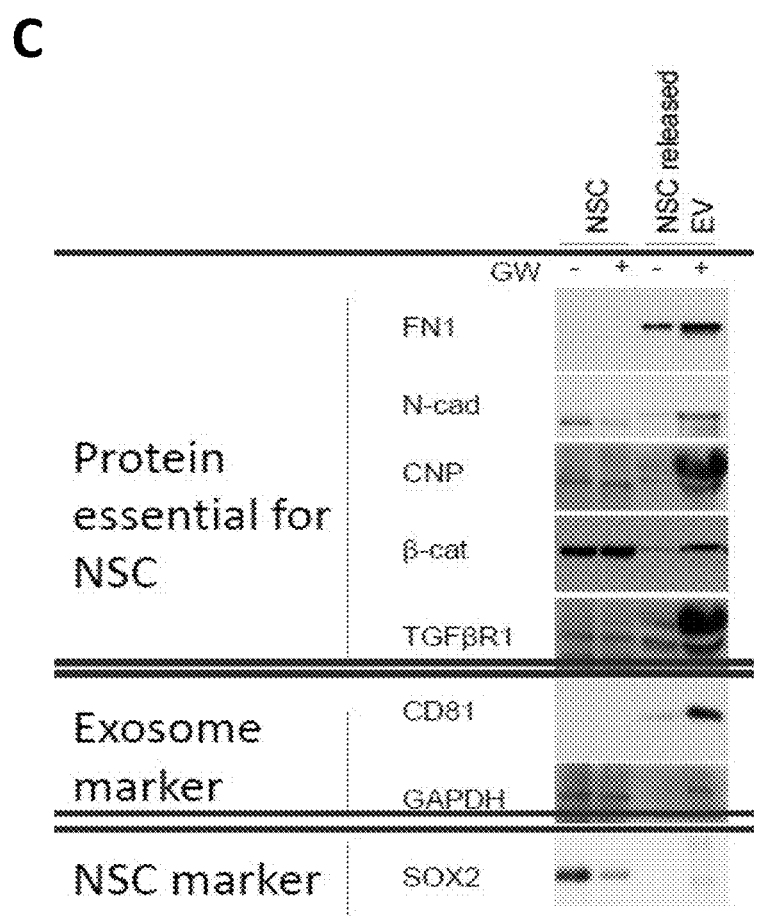

Similar results were obtained in GW-treated neural stem cells (NSCs). In the culture of GW-treated NSCs, the content of exosomal markers CD81 and GAPDH were increased (FIG. 10, C). The data suggested that blocking EP4-mediated signaling with EP4 antagonists increased EV/exosome release from neural stem cells and increased protein content of the EVs/exosomes required for maintaining stem cell homeostasis of NSCs (FIG. 10, C). In addition, it was found that the expression level of a NSC marker, SOX2, was much lower in GW-treated NSCs as compared to non-treated NSCs. This suggested that GW-treated NSCs lost their stem cell properties (FIG. 10, C).

Figure 12:
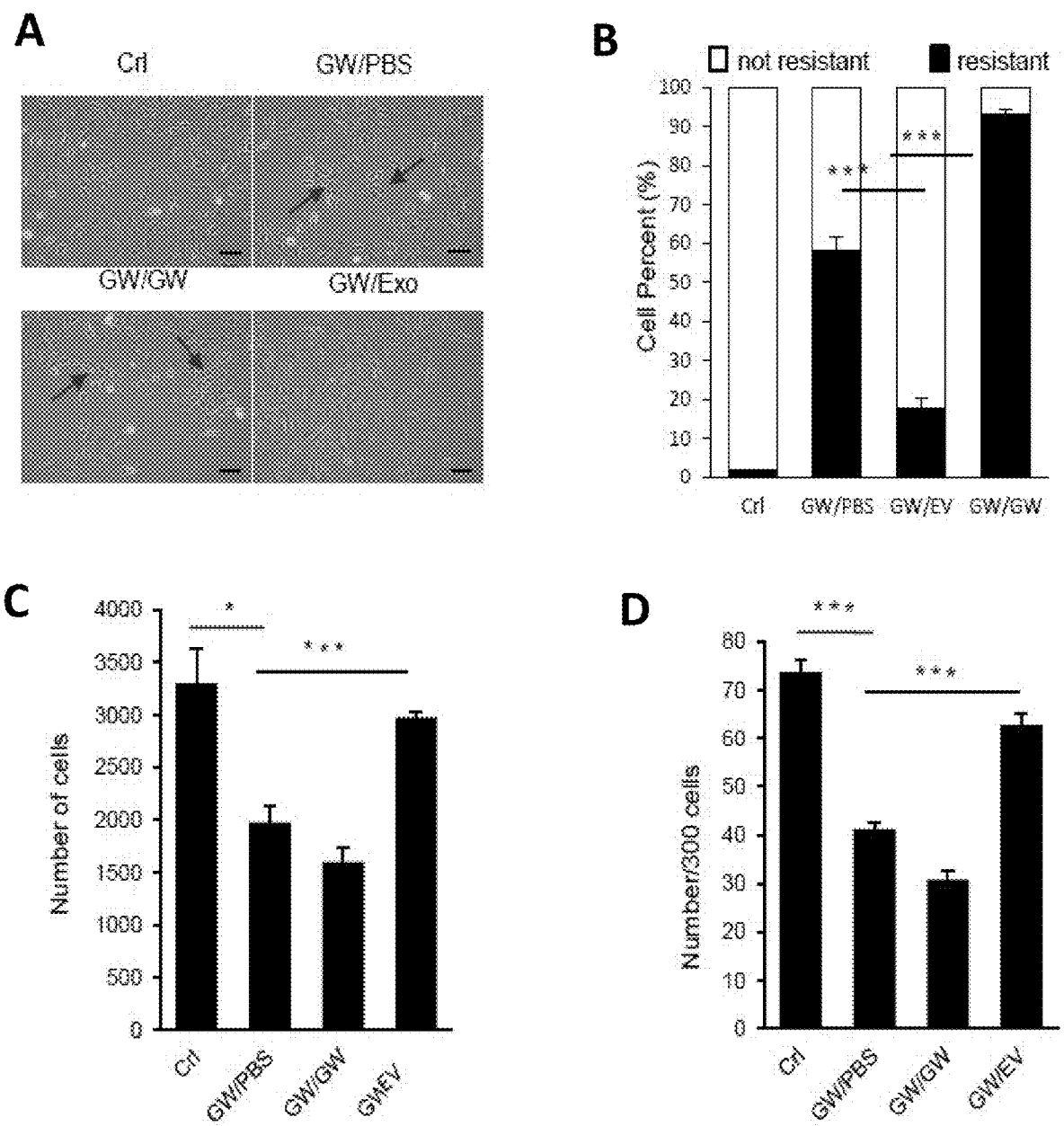
FIG. 12 shows analysis of GW-treated NAMECs subsequently treated with PBS (Crl) or with GW-induced exosomes. (A) is a set of bright-field images showing GW-treated NAMECs subsequently treated with PBS or with GW-induced NAMEC exosomes (1 μg/ml). Crl: treated with PBS for 8 days; GW/PBS: treated with GW for 4 days and then PBS for 4 another days; GW/GW: treated with GW for 8 days; GW/Exo: treated with GW for 4 days and then GW-induced NAMEC exosomes for another 4 days. Arrows: epithelial islands. Scale bar, 100 μm. (B) is a graph showing the percentage of GW-treated NAMECs subsequently treated with PBS (GW/PBS), with GW-induced NAMEC exosomes (1 μg/ml) (GW/Exo), or with GW a second time (GW/GW), that were resistant to 0.05% trypsin. "Crl" are data for PBS-treated NAMECs. NAMECs were treated as indicated, then dissociated with 0.05% trypsin. Data are means±SEM, (n=3). ***P≤0.005. (C) is a graph showing Boyden chamber migration of GW-treated NAMECs subsequently treated with PBS (Crl) or with GW-induced NAMEC exosomes. NAMECs were treated as indicated in (A). The treatment was suspended during the migration assay. Data are means±SEM (n=3). *P≤0.05. *P≤0.001. (D) is a graph showing mammosphere formation of GW-treated NAMECs subsequently treated with PBS (Crl) or with GW-induced exosomes. NAMECs were treated as indicated in (A). The treatment was suspended during the mammosphere assay. Data are means±SEM (n=4). *P≤0.001.

To further demonstrate the loss of the basal SC properties (including maintenance of stem cell homeostasis and migration ability) as a consequence of exosome formation, GW-treated NAMECs were cultured with GW induced exosomes from NAMECs (GW-in-NA exosomes) and observed for the reverse of EP4 antagonist-induced MET. As showed in FIG. 12, GW-treated NAMECs, when cultured with GW-in-NA exosomes, regained their mesenchymal phenotype (FIGS. 12, A and B), migration ability (FIG. 12, C) and mammosphere-forming ability (FIG. 12, D). The data suggested that capturing released exosomes allowed the EP4 antagonist-treated NAMECs to reacquire their SC properties.

Figure 20:
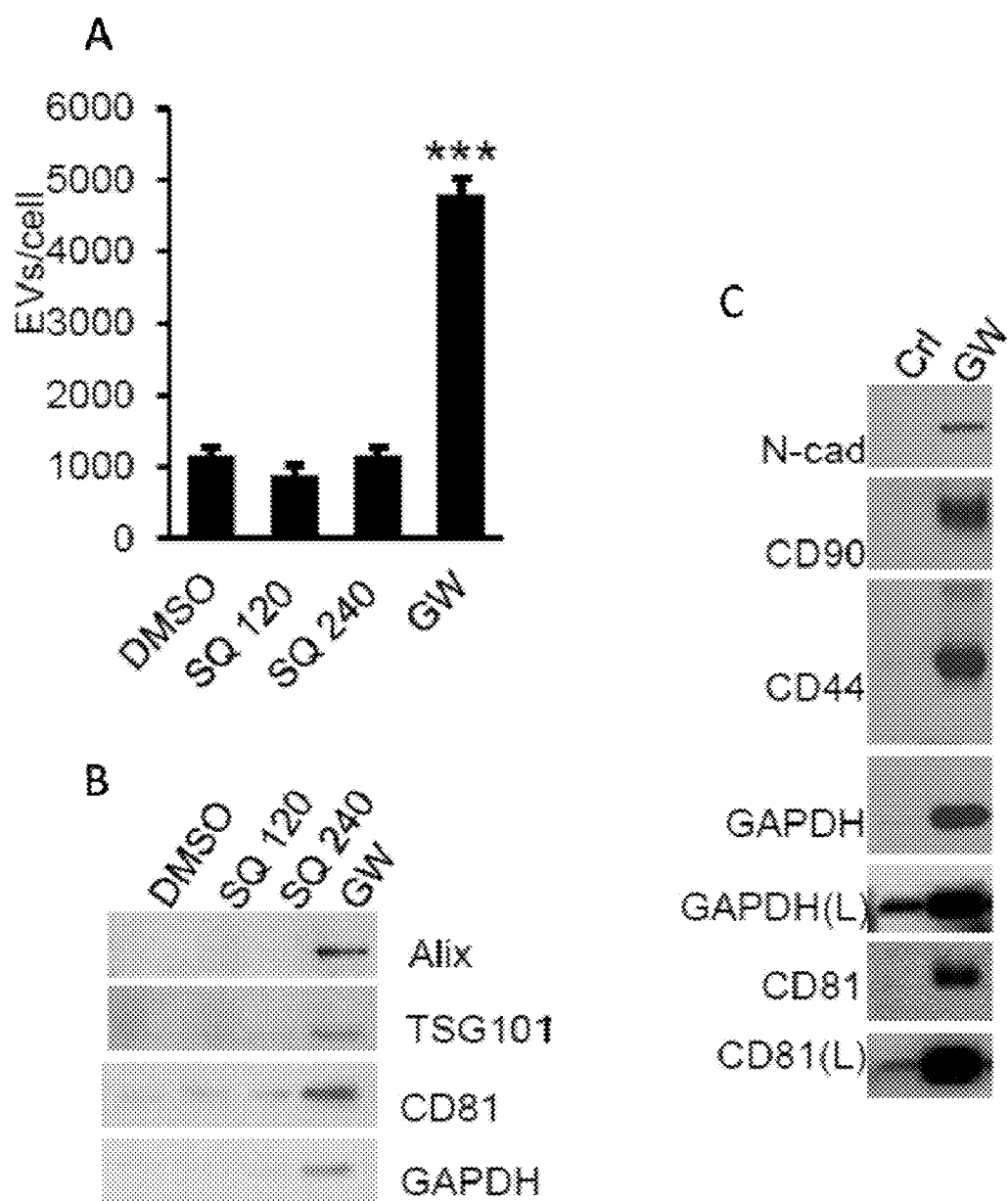
FIG. 20 shows that the EP4 antagonist GW decreased cancer stem cell/tumor initiating cell properties and induced EV/exosome release from Ras-transformed mammary epithelial stem cells (NAMEC-R) by specifically blocking PGE2/EP4 receptor-mediated signaling. (A) Quantification of EV/exosome release, shown as the number of particles present per cell in the CM-P4 fractions, from vehicle-treated NAMEC-R cells (Crl), GW627368X-treated NAMEC-R cells (GW, 1 μg/ml GW627368X for 4 days) and SQ 29,548-treated NAMEC-R cells (SQ120/SQ240; 120 nM and 240 nM for 4 days, TP antagonist as a negative control which does not induce exosome release). Vesicles in the P4 fractions were counted using NTA. Data are means±SEM (n=6). ***$P \leq 0.001$; (B) The Alix, TSG101, CD63, CD81 and GAPDH exosome markers were measured in the CM-P4 fractions of NAMEC-R cells treated with vehicle (Crl), GW627368X (GW, 1 μg/ml), SQ 29,548 (SQ120/SQ240; 120 nM and 240 nM); (C) The mesenchymal marker N-cadherin, CSC markers and exosome markers were analyzed in the conditioned medium P4 fraction derived from equal numbers of vehicle-treated NAMEC-R cells (Crl), GW-treated NAMEC-R cells (GW, 1 μg/ml GW627368X for 4 days) and SQ 29,548-treated NAMEC-R cells (SQ120/SQ240; 120 nM and 240 nM for 4 days). The longer GAPDH(L) and CD81(L) exposures show the low, but detectable, presence of GAPDH and CD81 in the conditioned medium P4 fraction of vehicle-treated NAMEC-R cells.

We further investigated whether EP4 antagonism and TP receptor antagonism (as GW has partial affinity to the human TP receptor) affected EV release from transformed mammary epithelial stem cells. Four-day conditioned media of vehicle, GW-, or SQ (a TP antagonist)-treated Ras-transformed NAMEC mammary stem cells (NAMEC-R) were collected and subjected to differential ultracentrifugation to isolate EVs released by the cells. The numbers of vesicles in CM-P4 fractions were determined using NTA (FIG. 20, A). EP4 antagonism elicited release of ~5000 vesicles per NAMEC-R cell. In contrast, only ~1000 vesicles per cell were released from vehicle-treated and SQ-treated NAMEC-R cells (FIG. 20, A). The EV/exosomal markers Alix, TSG101, CD81, and GAPDH were present in substantial amounts in the P4 medium fraction of GW-treated NAMEC-R cells (FIG. 20, B), suggesting that the GW EP4 antagonist triggered release of EVs/exosomes from NAMEC-R cells. In contrast, vehicle-treated and SQ-treated NAMEC-R cells produced only marginally detectable exosomal markers in the P4 fraction (FIG. 20, B). The mesenchymal marker N-cadherin and the cancer stem cell (CSC) markers CD90 and CD44 were also present in the EVs released by GW-treated NAMEC-R cells (FIG. 20, C). These data suggested that the removal of mesenchymal markers and CSC markers from EP4 antagonist-treated cancer cells via EVs/exosomes were responsible for the loss of CSC properties (e.g., mesenchymal phenotype, invasion ability, and tumorsphere-forming ability) by the EP4 antagonist-treated NAMEC-R cells. Furthermore, these changes result from the specific blockage of PGE2/EP4 signaling by EP4 antagonist GW, not from TP receptor-mediated signaling.

Figure 21:
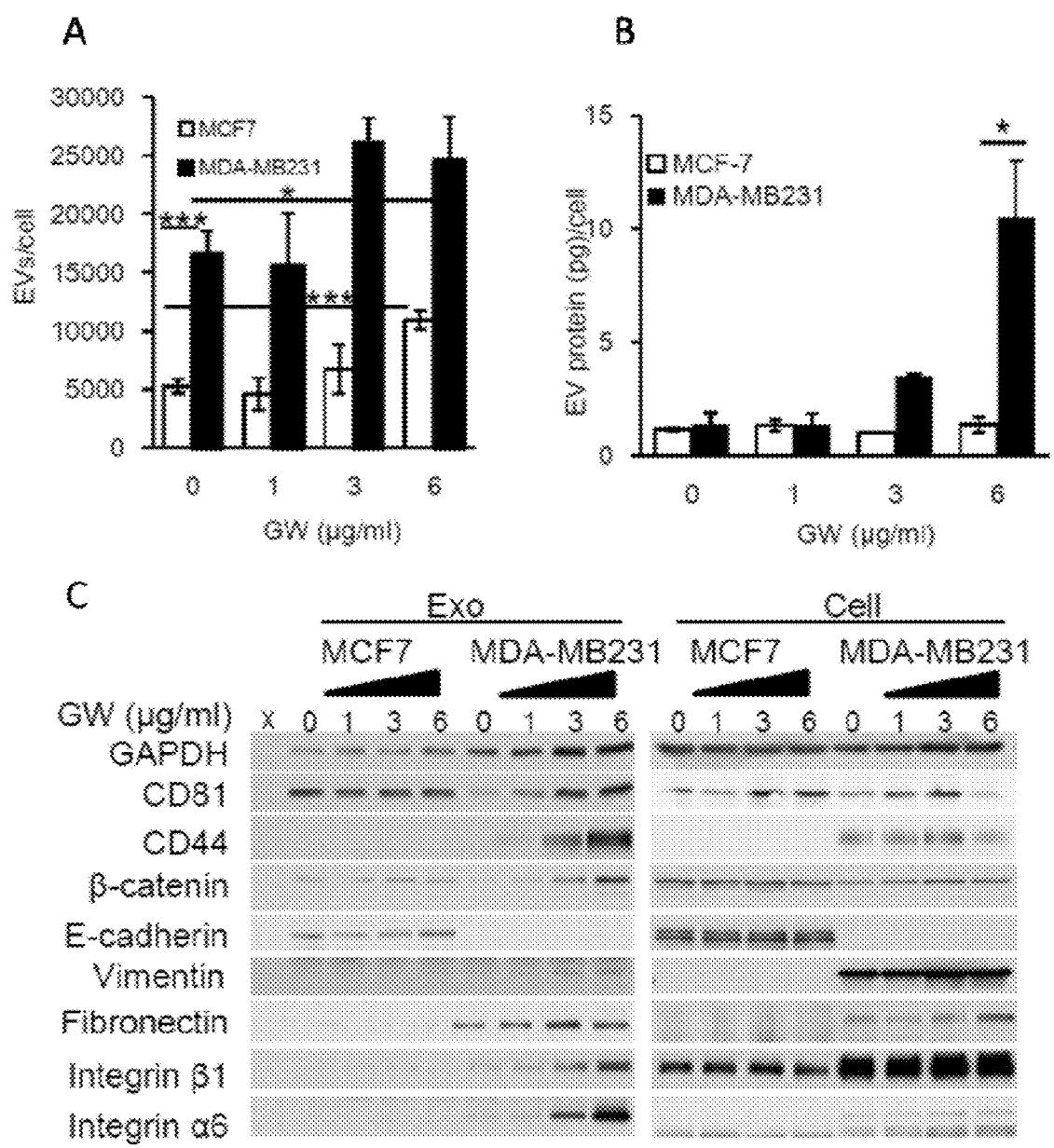
FIG. 21 shows that the EP4 antagonist GW caused cancer stem cell protein release from $CD44^{hi}/CD24^-$ human carcinoma stem cells via EVs/exosomes. (A) Quantification of EV/exosome release, shown as the number of particles in the CM-P4 fractions released per cell, from MCF-7 and MDA-MB-231 breast cancer cells treated with vehicle or with the indicated concentrations of GW627368X. Particles in the P4 fractions were counted using nanoparticle tracking analysis. Data are means±SEM (n=10). *$P \leq 0.05$, ***$P \leq 0.001$. (B) Quantification of the total EV protein released from MCF-7 and MDA-MB-231 cells treated with vehicle or with the indicated concentrations of GW627368X. The amounts (m) of protein present per cell in the conditioned medium P4 fractions are presented as means±SEM (n=3). *$P \leq 0.05$; (C) Protein levels in the P4 EV/exosome fractions and cell lysates, analyzed by Western blot. Culture media and cell lysates were collected from the same numbers of MCF-7 and MDA-MB-231 cells treated with vehicle or with GW627368X (GW), at the indicated concentrations, for 4 days. The P4 fractions of the culture media, containing EVs, were isolated. Negative control: "X": P4 fraction of blank culture medium.

We next examined whether blocking EP4-mediated signaling with an EP4 antagonist can elicit EV-mediated removal of CSC proteins (e.g., mesenchymal markers and stem cell markers) in the human breast carcinoma MCF-7 and MDA-MB-231 cell lines. P4 fractions from the conditioned media (CM-P4) of GW-treated MCF-7 and MDA-MB-231 cells were analyzed using NTA (FIG. 21, A). The CM-P4 fractions contained vesicles ranging from 40-130 nm. The sizes of the vesicles released by MCF-7 and MDA-MB-231 cells corresponded with that of exosomes (50-150 nm). Treatment of MCF-7 and MDA-MB-231 cells with increasing concentrations of the GW EP4 antagonist modestly increased the numbers of EVs released by both cell types (FIG. 21, A). However, the amount of protein per cell in the EV/exosome fraction was 10-fold greater for GW-treated "mesenchymal-like" MDA-MB-231 cells (FIG. 21, B).

EP4-agonist-induced EVs/exosomes from "mesenchymal-like" MDA-MB-231 breast cancer cells and from "epithelial-like" MCF-7 breast cancer cells contained some proteins in common, e.g., the exosomal marker CD81 and GAPDH proteins (FIG. 21, C). However, EP4 antagonist-induced EV proteins from MDA-MB231 "mesenchymal-like" cells were enriched in CSC markers (e.g., CD44 and β-catenin), in mesenchymal markers (e.g., vimentin and fibronectin), and in integrins (e.g., integrin β1 and integrin α6) when compared to the proteins present in EP4 antagonist-elicited EVs/exosomes from "epithelial-like" MCF-7 cells (FIG. 21, C). Thus, as observed for NAMEC-R cells (FIG. 20, A-C), blocking EP4-mediated signaling induced the release of EVs (e.g., exosomes) and EV-associated CSC-related proteins from stem-like MDA-MB-231 human breast carcinoma cells.

Based on the results described above, the released EVs/exosomes induced by an EP4 antagonist uniquely carry proteins/miRNAs required for maintaining stem cell homeostasis. The induced EVs/exosomes can make the stem cells lose their original stem cell properties and transfer stem cell properties to non-stem cells.

Example 3. Exsosomes Released by EP4 Antagonist Induction can Induce Non-Stem Tissue Cell to Transform to Stem Cell by Reprogramming EP4 antagonist-induced exosomes from basal mammary epithelial stem cells (NAMECs) increased migration and mammosphere formation of HMLE epithelial non-stem cell counterparts.

Figure 13:
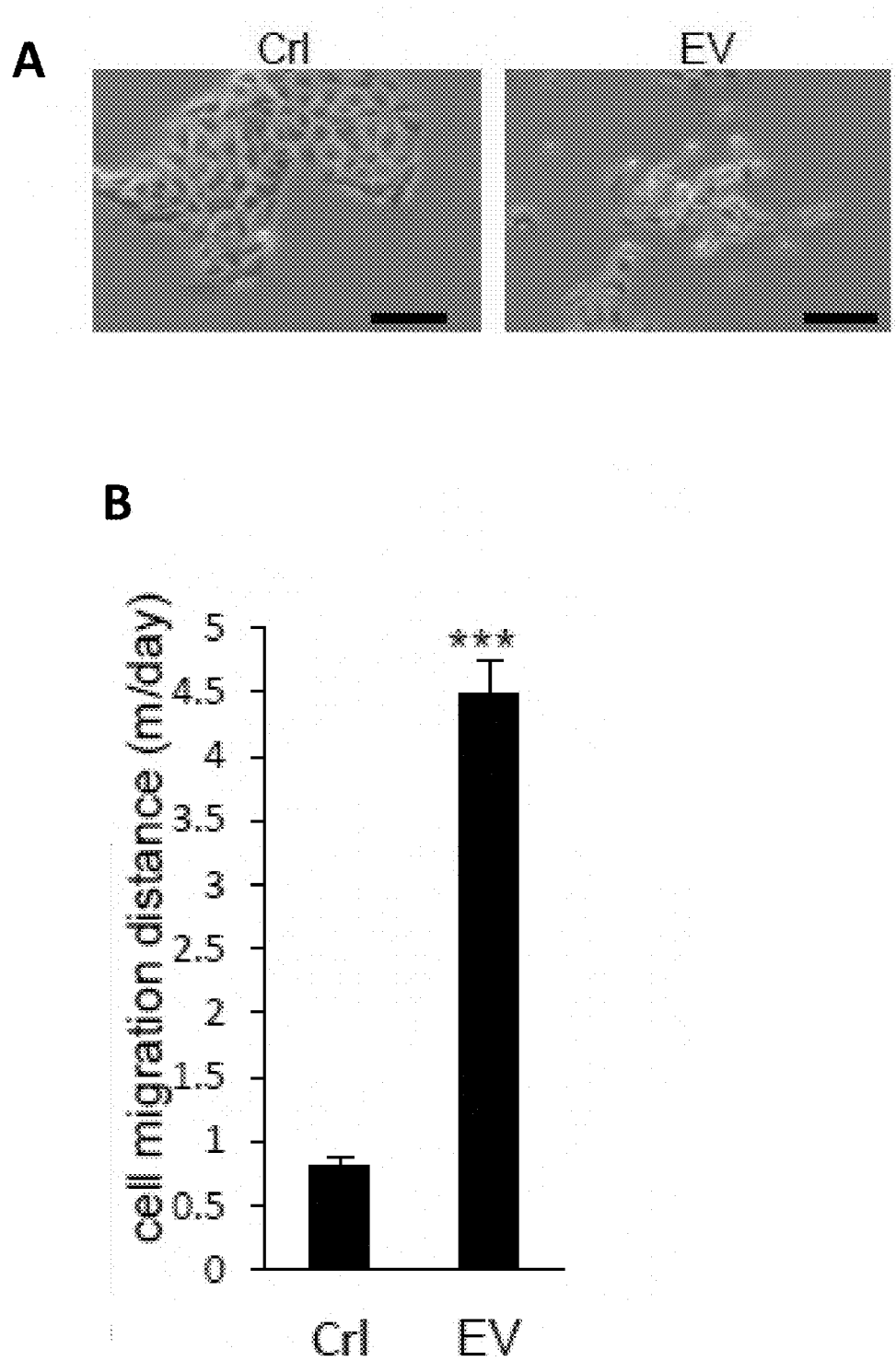
FIG. 13 shows an analysis of HMLE cells pre-treated with PBS (Crl) or 1 μg/ml GW627368X(GW)-induced NAMEC exosomes (EVs). (A) is a set of bright-field images of HMLE cells pre-treated with PBS (Crl) or 1 μg/ml GW-induced NAMEC exosomes (EV). Fresh exosomes (1 μg/ml) and medium were supplied every two days for 2 weeks. Cells were split every 4 days. The images (taken 14 days after initiation of PBS or exosome treatment) are excerpts from the time-lapse movies. Scale bar, 100 μm. (B) is a graph showing migration of HMLE cells pretreated with PBS (Crl) or GW-induced NAMEC exosomes (EV). Cell migration was tracked for 24 hours using time-lapse imaging. The average lengths of the migration tracks are plotted. Data are means±SEM (n=20). ***P≤0.001. (C) is a graph showing Boyden chamber migration of HMLE cells treated with PBS or GW-induced NAMEC EVs. HMLE cells were treated as follows: HMLE+Exo: 1 μg/ml exosomes were added during the 72-hour migration assay; Exo-HMLE: HMLE were pre-treated with exosomes for 7 days and the drug treatment was suspended during the migration assay. Data are means±SEM (n=3). *P≤0.05. **P≤0.005. (D) is a graph showing mammosphere formation of HMLE cells treated with PBS or GW-induced NAMEC EVs for 7 days. The treatment was suspended during the mammosphere assay. Data are means±SEM (n=5). *P≤0.05.
Figure 13:
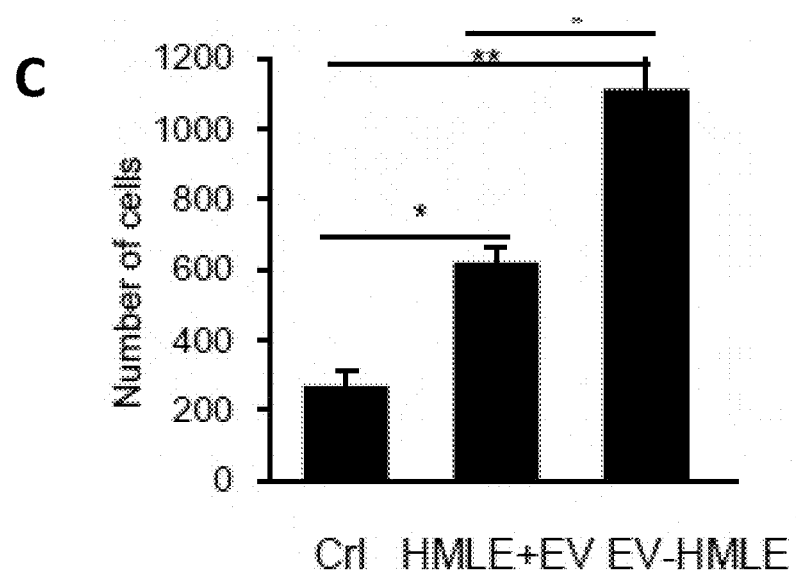
Figure 13:
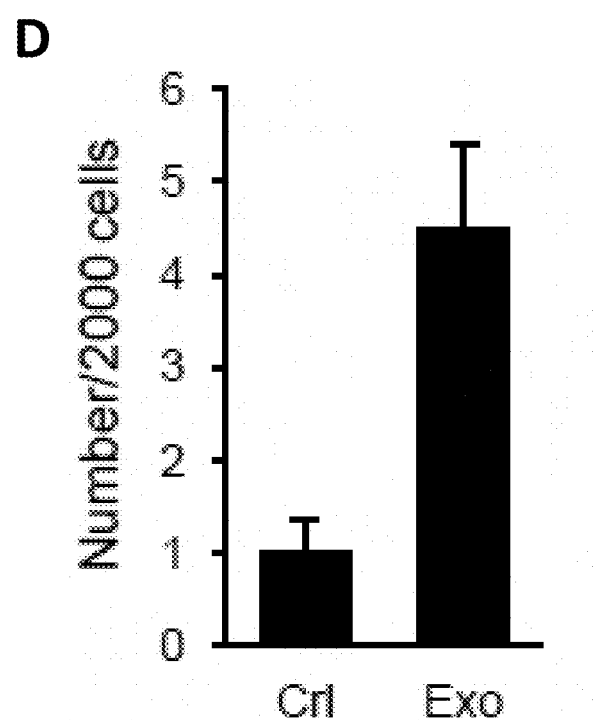

To determine whether uptake of SC-released exosomes can turn non-stem cells into stem cells, HMLE cells, non-stem cells, were cultured with GW-in-NA exosomes for 7 days and then analyzed for stem cell properties in the absence of further exosome treatment. GW-in-NA exosomes induced morphological changes of non-stem cells; morphologically distinguishable mesenchymal subpopulations appeared in the GW-in-NA exosome-treated HMLE cells. See, FIG. 13, A. These GW-in-NA exosome-treated HMLE cells were more migratory than the control HMLE cells. In contrast, the vehicle-treated HMLE cells rarely migrated. The mean migration distance of the GW-in-NA exosome-treated HMLE cells was six-fold greater than that of HMLE cells (FIG. 13, B). The data suggest that uptake of GW-in-NA exosomes promotes a morphological EMT of HMLE cells and increases their migration ability.

In addition, the number of migrating cells of HMLE non-stem cells was increased about 4-fold (FIG. 13, C) and the number of mammospheres formed by the HMLE non-stem cells was increased about 3-fold by the GW-in-NA exosome pretreatment for two weeks (FIG. 13, D). The results suggested that uptake of EP4 antagonist-induced basal SC exosomes could increase migration ability and mammosphere-forming ability of non-stem mammary epithelial cells.

EP4 Antagonist-Induced Exosomes Transfer Mammary Gland-Forming Ability to Primary Mammary Luminal Cells To evaluating whether EP4 antagonist-induced exosomes were able to convert luminal cells to mammary gland-forming stem cells, so called mammary repopulating units (MRUs), primary mouse mammary epithelial cells were isolated from fat pads for sorting luminal cells and for generating EP4 antagonist-induced exosomes. Mouse EpCAM$^{lo}$/CD49f$^{hi}$ mammary basal stem cells and EpCAM$^{hi}$/CD49f$^{lo}$ luminal non-stem cells were sorted using the differential expression of epithelial cell adhesion molecule (EpCAM) and integrin α6 (CD49f). In addition, PGE2-induced and GW-induced exosomes were collected from mouse primary mammary epithelial cells.

Figure 14:
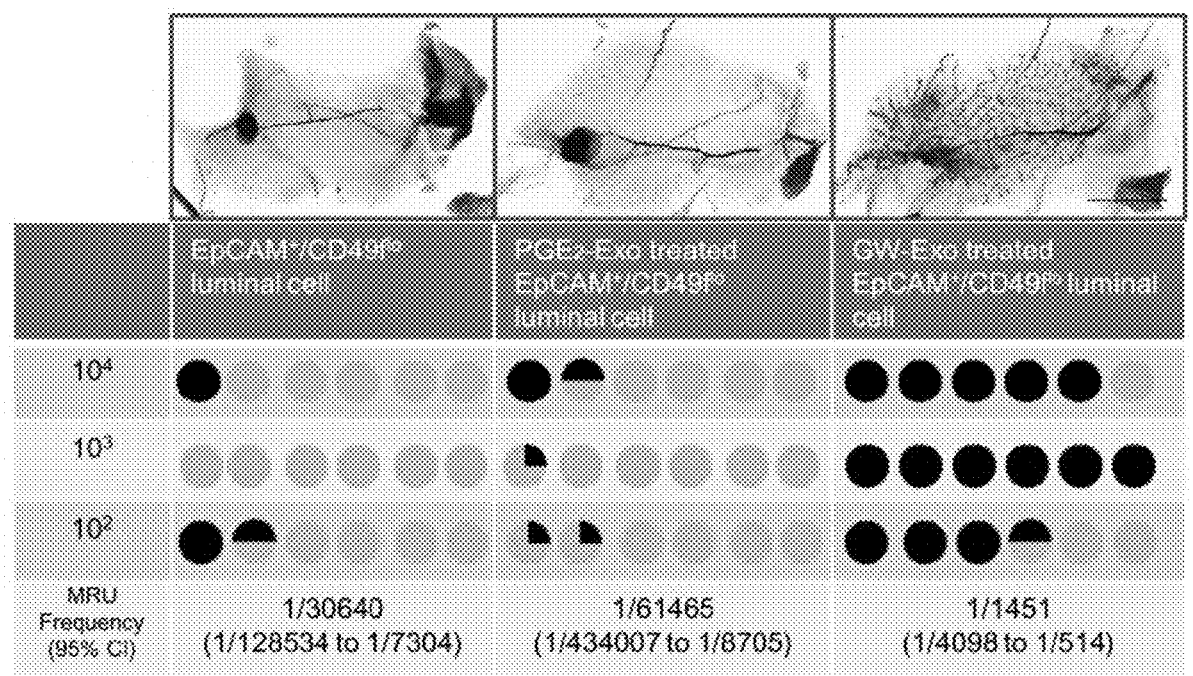
FIG. 14 shows mammary gland formation by primary mouse mammary cells. Primary mouse EpCAM$^{hi}$/integrin α6(CD49f)$^{lo}$ luminal cells were treated with PGE2-induced or GW-induced exosomes from mouse primary mammary epithelial cells or GW-in-NA Exo (1 μg/ml) in cell culture for 10 days. After the treatment, the cells were implanted at the numbers per pad shown in the table, into the cleared fat-pads of 3-week-old mice. Mice were euthanized and necropsied after 8 weeks to analyze mammary gland formation. Grey spot: an injected pad with no gland formation. Black spot: an injected pad with completed gland formation. Partial black spot: an injected pad with partial gland formation. Mammary repopulating unit (MRU) frequencies were calculated using Extreme limiting dilution analysis (ELDA). Scale bar, 0.75 cm.

As showed in FIG. 14, MRU frequency of EpCAM$^{hi}$/integrin α6 (CD490$^{lo}$ luminal non-stem cells (gland-forming efficiency: 1/6, 0/6, <2/6) were low. The MRU frequency of EpCAM$^{hi}$/CD49f$^{lo}$ luminal non-stem cells (gland-forming efficiency: 5/6, 6/6, <4/6) was increased ~20-fold by GW-induced SC exosome pre-treatment for 10-days (gland-forming efficiency: <2/6, <1/6, <2/6). These results suggested that EP4 antagonist-induced mammary epithelial stem cell exosomes could transfer mammary repopulating ability to the luminal non-stem cells.

EP4 antagonist-induced basal stem cell exosomes transferred stem cell properties via lipid raft-associated factors.

To verify whether the lipid raft-associated factors were responsible for the ability of EP4 antagonist-induced basal stem cell exosomes to transfer stem cells properties, HMLE non-stem cells were cultured with the same numbers of GW-, PGE2- or GW+MβCD-induced NAMEC exosomes (called as GW-in-NA Exo, PGE2-in-NA Exo, or GWMβ-in-NA Exo), and observed the migration ability and mammosphere-forming ability of treated cells. It was shown that the number of migrating cells of HMLE cells was increased ~10-fold by GW-in-NA exosomes pre-treatment, while PGE2-in-NA exosomes only increased the number of migrating cells to 3-fold. See, FIG. 15, A. In addition, the effect of GWMβ-in-NA exosomes on increasing migrating cells was significantly decreased, compared to GW-in-NA control exosomes.

Figure 15:
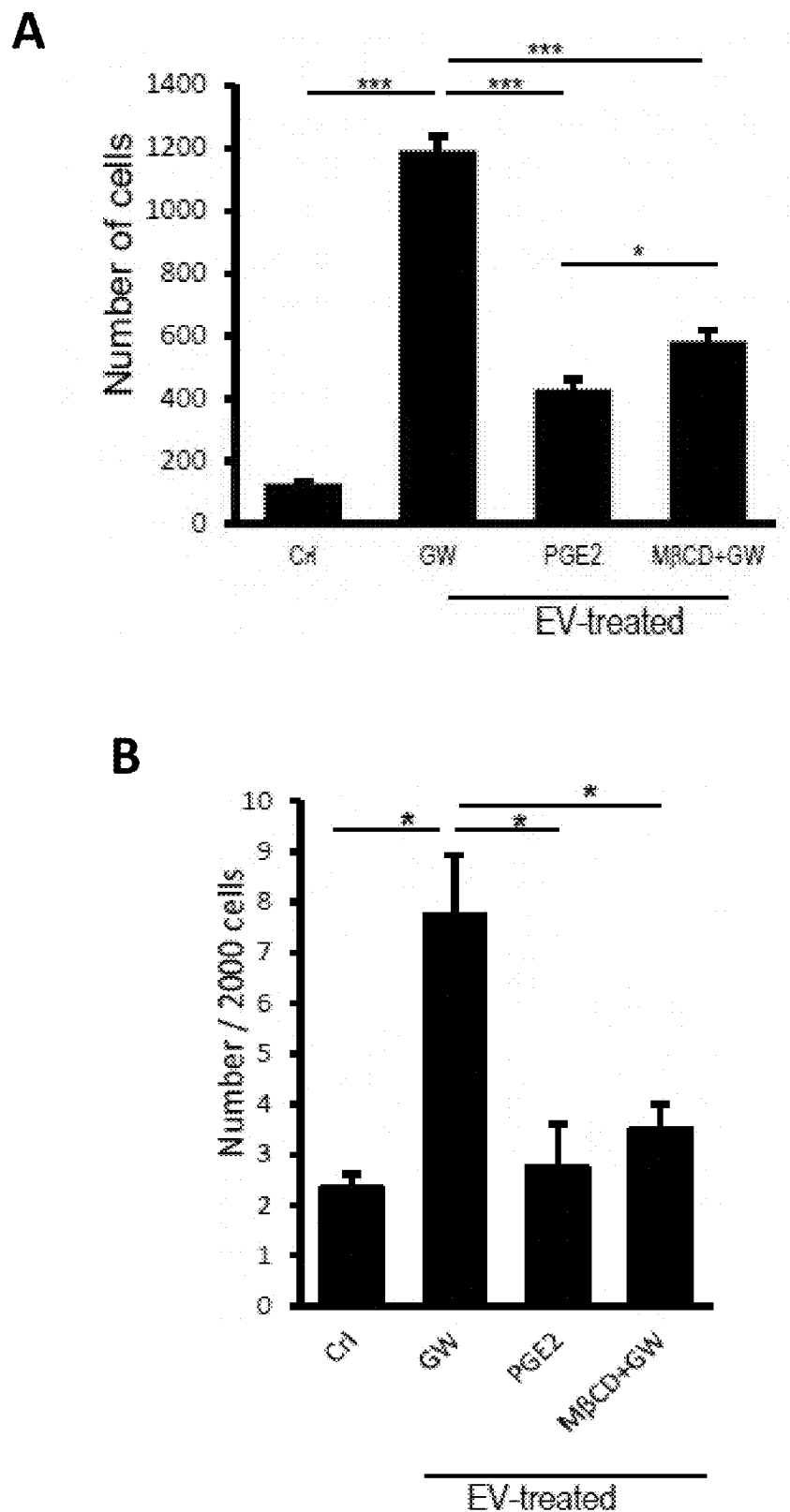
FIG. 15 shows cells pre-treated with PBS (Crl), GW-in-NA Exo (1 μg/ml), PGE2-in-NA Exo (2 μg/ml), or GWMβ-in-NA Exo (1 μg/ml). (A) shows Boyden chamber migration of HMLE cells pre-treated with PBS, GW-in-NA Exo, PGE2-in-NA Exo (2 μg/ml), or GWMβ-in-NA Exo for 7 days. The drug treatment was suspended during the migration assay. Data are means±SEM (n=3). *P≤0.05. **P≤0.005. (B) shows mammosphere formation of HMLE cells pre-treated with PBS, GW-in-NA Exo, PGE2-in-NA Exo, or GWMβ-in-NA Exo for 7 days. The treatment was suspended during the mammosphere assay. Data are means±SEM (n=5). *P≤0.05. (C) shows mammary gland formation by primary mouse mammary cells. Primary mouse EpCAM$^{hi}$/integrin α6 (CD490$^{lo}$ luminal cells were treated with PBS, GW-in-NA Exo (1 μg/ml), PGE2-in-NA Exo (2 μg/ml), or GWMβ-in-NA Exo (1 μg/ml) in vitro for 10 days. After the treatment, the cells were implanted at the indicated numbers per pad into the cleared fat-pads of 3-week-old mice. The mice were euthanized and necropsied after 8 weeks to analyze mammary gland formation. Grey spot: an injected pad with no gland formation. Black spot: an injected pad with completed gland formation. Partial black spot: an injected pad with partial gland formation. MRU frequencies were calculated using ELDA. Scale bar, 0.75 cm.
Figure 15:
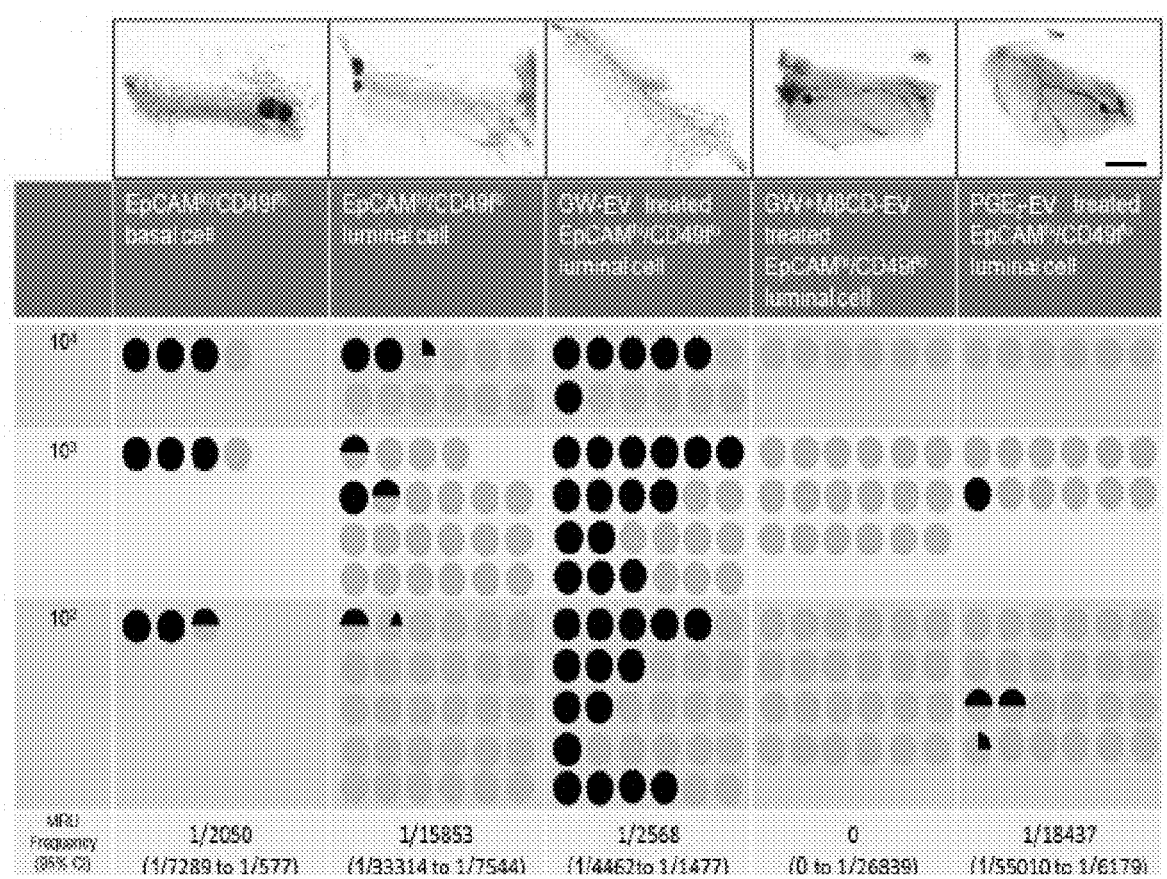

Similarly, the number of mammospheres formed by the HMLE cells was increased ~4-fold by the GW-in-NA exosome pre-treatment for 7 days, while both PGE2-in-NA exosomes and GWMβ-in-NA exosomes did not have an effect on mammosphere formation (FIG. 15, B). The results suggested that uptake of EP4 antagonist-induced basal stem cell exosomes could increase migration ability and mammosphere-forming ability of mammary epithelial non-stem cells largely via lipid raft-associated factors in the exosomes.

In addition, the lipid raft-associated factors in EP4 antagonist-induced basal stem cell exosomes is required for transfer of mammary gland-forming ability to luminal cells. The MRU frequency of EpCAM$^{lo}$/CD49f$^{hi}$ basal cells (gland-forming efficiency: 3/4, 3/4, 3/3) was seven fold greater than that of EpCAM$^{hi}$/CD49f$^{lo}$ luminal cells (gland-forming efficiency: 3/12, 3/22, 2/30). See, FIG. 15, C. While the luminal cells rarely formed mammary glands, the 10-day GW-in-NA exosome pre-treatment prior to the implantation converted them into cells capable of efficiently forming mammary glands (gland forming efficiency: 6/12, 15/24, 15/30). The MRU frequency of the luminal cells was increased ~6-fold by GW-in-NA exosome pre-treatment, reaching the MRU frequency of mouse mammary gland basal cells. While EP4 antagonist-induced basal stem cell exosomes could transfer mammary repopulating ability to the luminal cells, PGE2-in-NA exosomes (gland-forming efficiency: 0/6, 0/18, 0/24) and GWMβ-in-NA exosomes (gland-forming efficiency: 0/6, 1/12, 3/24) could not increase MRU frequency of the luminal cells. These results suggested that the ability of EP4 antagonist-induced stem cell exosomes to transfer mammary repopulating ability to luminal cells depended on the lipid-raft associated factors in the exosomes.

Converted neuroectodermal cells via taking up EP4 antagonist-induced MSC exosomes (MSCGWEVs) exhibited NSC properties—neuronsphere forming ability.

Figure 16:
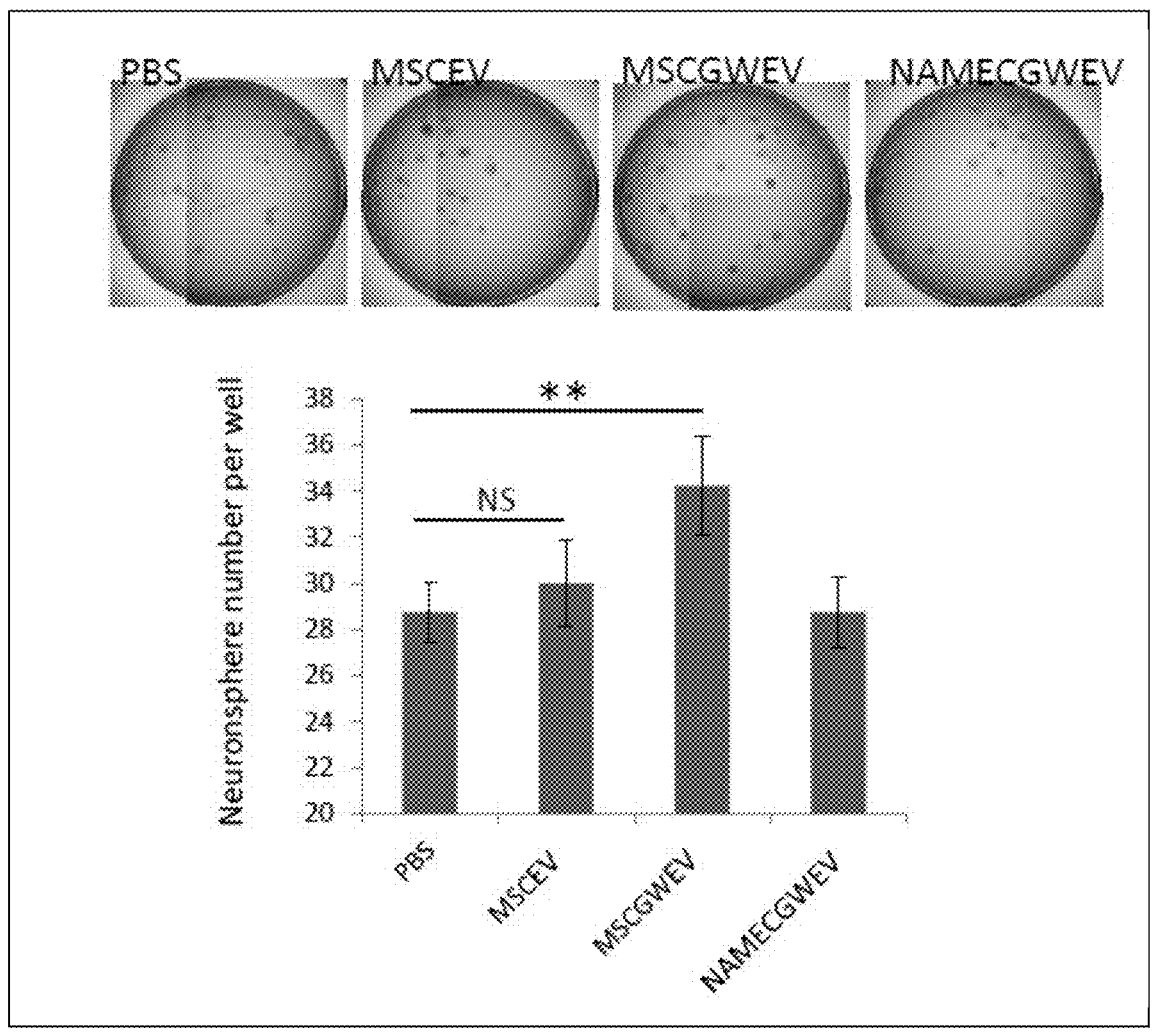
FIG. 16 shows that EP4 antagonist-induced MSC EVs could increase NSC properties such as neuronsphere forming ability. Neuronsphere formation of NE4C cells treated with PBS (Crl), MSC EVs, GW-induced MSC EVs, or GW-induced NAMEC EVs was determined using neuronsphere analysis. The treatment was suspended during the Neuronsphere assay. Data are means±SEM (n=5). **$P \leq 0.01$.

EP4 antagonist-induced MSC EVs/exosomes (MSCGW-EVs) were applied to neural tissue to convert non-stem cells into neural stem cells having ability to differentiate into neurons. As showed in FIG. 16, the co-culture of neuroectodermal cells with EP4 antagonism-induced MSC EVs/exosomes (MSCGWEVs) increased the number of neural stem cells as measured by neuronsphere formation. The data suggested that EP4 antagonist-induced MSC EVs/exosomes (MSCGWEVs) transferred the stem cell properties to neuroectodermal cells that did not have stem cell properties. The neuroectodermal cells taking up EP4 antagonist-induced MSC EVs/exosomes (MSCGWEVs) further convert to neural stem cells (NSCs).

Figure 17:
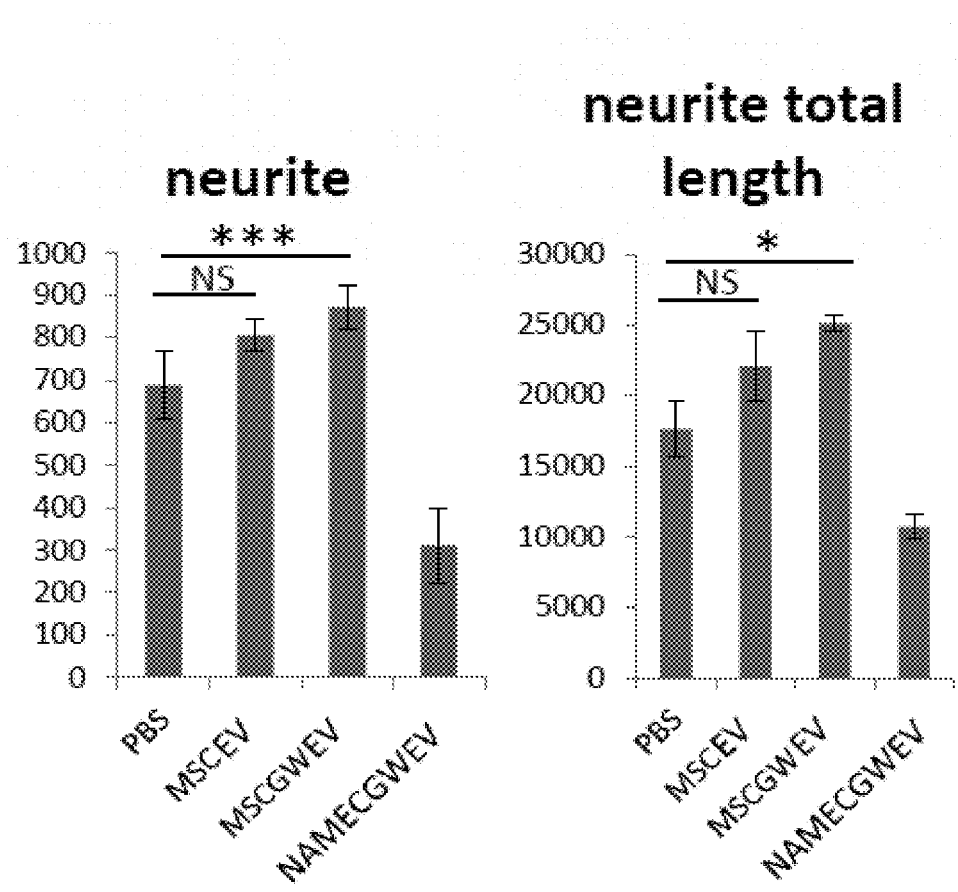
FIG. 17 shows that EP4 antagonist-induced MSC EVs could increase neuron differentiation from neuroectodermal cells. NE-4C neuroectodermal cells, which were pretreated with PBS, MSC EVs, GW-induce MSC EVs, or GW-induced NAMEC EVs, were treated with retinoic acid (RA) to induce neuron differentiation. After the RA treatment, the induced neurons were stained with anti-beta3-tubulin antibody. The numbers and lengths of neurites were quantified and plotted. Data are means±SEM (n=4). *$P \leq 0.05$, ***$P \leq 0.001$.

NE-4C neuroectodermal cells, which were pretreated with PBS, MSC EVs/exosomes (MSCEVs), GW-induce MSC EVs/exosomes (MSCGWEVs), or GW-induced NAMEC EVs/exosomes (NAMECEVs), were treated with retinoic acid (RA) to induce neuron differentiation. After the RA treatment, the induced neurons can be stained with anti-beta3-tubulin antibody. The result as shown in FIG. 17 indicated that the neuroectodermal cells, which were pretreated with GW-induced MSC EVs/exosomes, could differentiate into neurons with more neurites and longer neurites. The data suggested that uptake of EP4 antagonist-induced MSC EVs/exosomes by neuroectodermal cells increased potential of the cells to differentiate into neurons.

Figure 18:
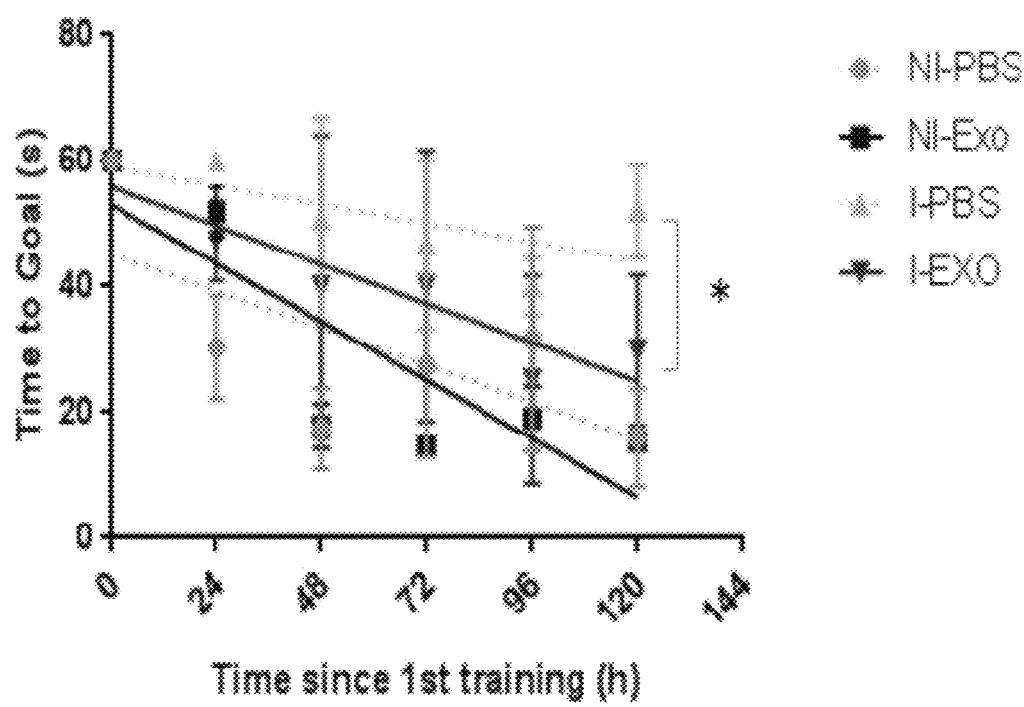
FIG. 18 shows the learning and memory abilities of mice with hippocampal damages treated with PBS or EP4 antagonist-induced MSC exosomes (EXO), evaluated using Morris water maze. Learning and memory were evaluated by time cost for finding the goal after the training. NI-PBS: PBS treated normal mice, NI-Exo: EP4 antagonist-induced-MSC-exosome treated normal mice, I-PBS: PBS treated damaged mice, I-EXO: EP4 antagonist-induced-MSC-exosome treated damaged mice.
Figure 22:
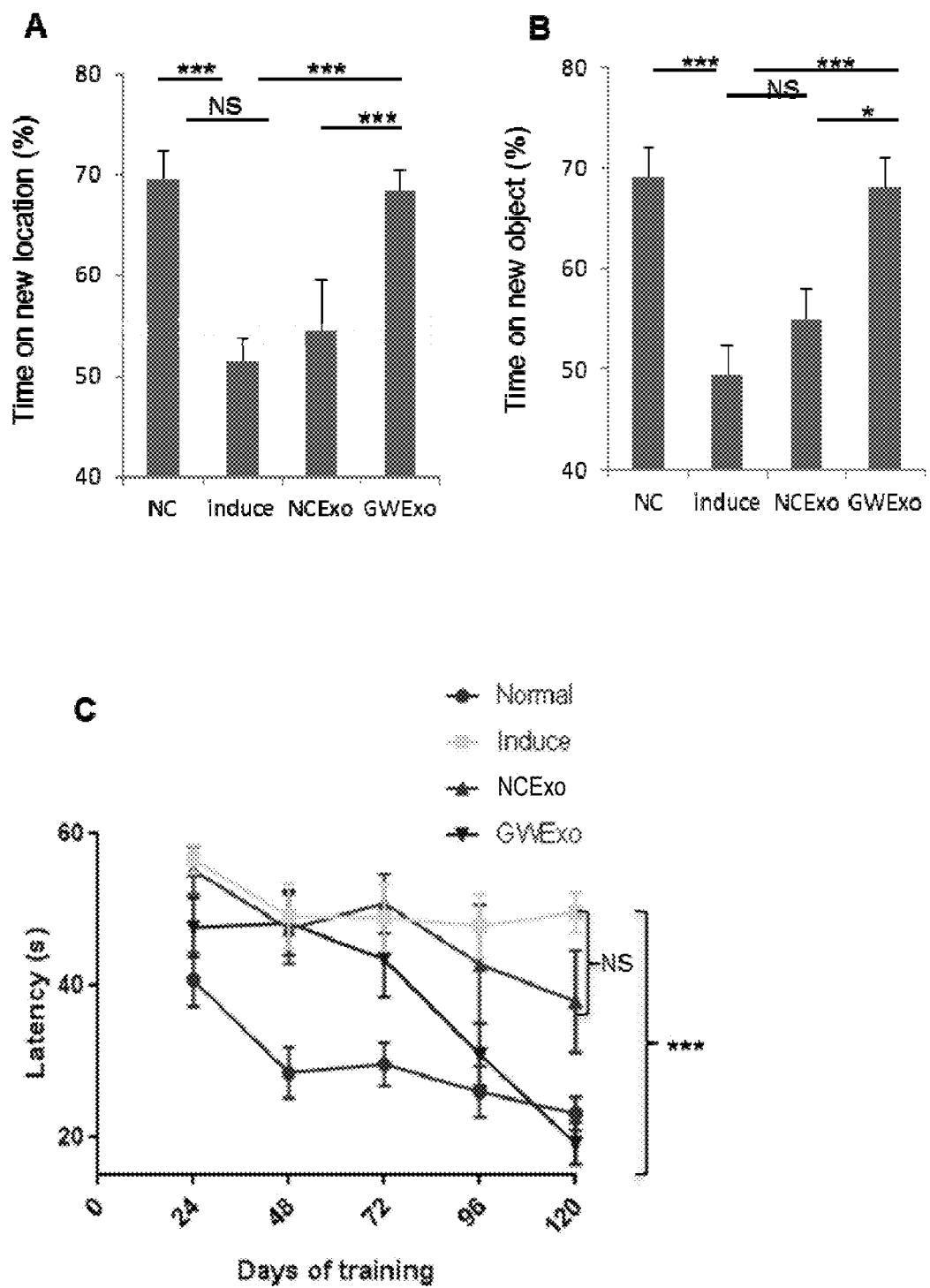
FIG. 22 shows that the learning and memory defects in mice with hippocampal damages could be rescued by EP4-antagonist-induced MSC-derived EVs/exosomes. Learning and memory of mice were evaluated using (A) novel location recognition test (NLRT), (B) novel object recognition test (NORT), and (C) Morris water maze. NC: normal mice; Normal: normal mice; Induce: mice with hippocampal damages; NCExo: damaged mice treated with exosomes isolated from MSCs not treated with an EP4 antagonist; GWExo: damaged mice treated with EP4 antagonist-induced MSC exosomes. *$P \leq 0.05$, ***$P \leq 0.001$.
Figure 23:
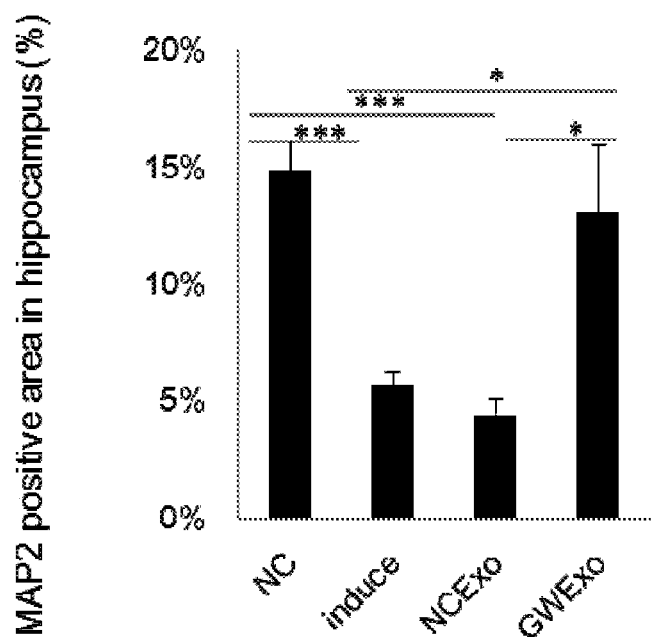
FIG. 23 is a set of graphs showing that neuron regeneration (A) and inflammation suppression (B) in mouse brains with hippocampal damages could be triggered by EP4-antagonist-induced MSC EVs/exosomes. The brain neuron regeneration was evaluated by measuring neuronal cell marker MAP2 in the hippocampus (A). The inflammation was reflected by the numbers of microglia in the hippocampus (B). NC: normal mice; Normal: normal mice; Induce: mice with hippocampal damages; NCExo: non-induced MSC-exosome-treated damaged mice; GWExo: EP4-antagonist-induced-MSC-exosome treated damaged mice. *$P \leq 0.05$, $P \leq 0.005$, *$P \leq 0.001$.
Figure 23:
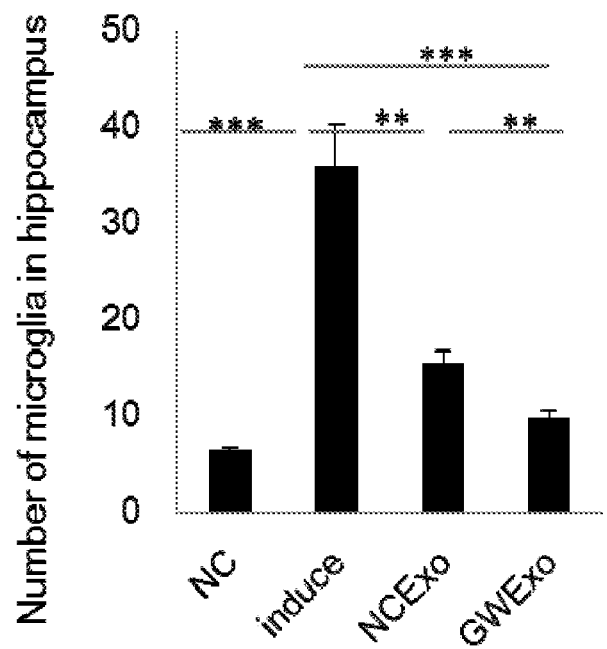

Example 4. EP4 Antagonist-Induced Mesenchymal Stem Cell (MSC)-Derived EVs/Exosomes Rescued Defects of Cognition, Learning, and Memory Caused by Hippocampus Degeneration Learning and memory of the mice with (I-PBS and, I-EXO in FIG. 18; induce, NCexo and GWExo in FIG. 22, C) and without (NI-PBS and NI-EXO in FIG. 18 and NC in FIG. 22, C) hippocampal damages were evaluated using Morris water maze in this example. Learning and memory were evaluated by time cost for finding the goal after the training. It was found that learning and memory ability of the damaged mice treated with GW-induced MSC exosomes (I-EXO in FIG. 18 and GWExo in FIG. 22, C) are significantly better than that of PBS-injected damaged mice (I-PBS in FIG. 18 and induce in FIG. 22, C) and that of damaged mice treated with non-induced MSC exosomes (NCExo in FIG. 22, C), as showed in FIG. 18 and FIG. 22, C. The rescue of cognition was further verified by additional cognitive tests (novel location recognition test and novel object recognition test). See, FIGS. 22, A and B. We also showed that GW-induced exosomes from MSCs were able to induce neuron regeneration in the brains of mice with hippocampal damages by visualizing the neuronal cells, perikarya dendrites, and neuronal dendrites in brain tissues using the MAP2 neuronal cell marker (FIG. 23, A) and beta3-tubulin neuronal cell marker (data not shown). We also showed that GW-induced exosomes from MSCs were able to suppress inflammation in the brains of mice with hippocampal damages by visualizing the decrease of microglia, macrophages of the central nervous system, using the Iba1 microglia marker (FIG. 23, B). Suppression of inflammation in damaged brains also helps brain neuronal cell regeneration. These combined data demonstrated the therapeutic efficacy of EP4-antagonist-induced EVs/exosomes on neurodegenerative disease caused by hippocampus degeneration, such as Alzheimer disease and Parkinson disease.

The invention claimed is:

1. A method of producing exosomes enriched for proteins and mRNAs for maintenance of stem cell properties or for cell regeneration, the method comprising:

obtaining an isolated population of stem cells, wherein the stem cells are mesenchymal stem cells, mammary epithelial stem cells, neural stem cells or cancer stem cells, culturing the isolated population of stem cells in a culture medium suitable for culturing the stem cells, wherein the culture medium contains an amount of a prostaglandin E receptor 4 (EP4) antagonist effective for inducing release of exosomes enriched for proteins and miRNAs for maintenance of stem cell properties or for cell regeneration from the stem cells, for a sufficient period of time to allow release of the exosomes, whereby the exosomes are released from the stem cells into the culture medium, and isolating the exosomes from the culture medium, wherein the exosomes have a diameter of 50 nm to 150 nm, wherein one or more of said exosomes express a higher level of one or more exosome markers HSP70, CD81, TSG101, Alix, CD9, and GAPDH, and have a higher protein and miRNA content for maintenance of stem cell properties or for cell regeneration, as compared to control stem cells not treated with an EP4 antagonist.

2. The method of claim 1, wherein the stem cells are cultured for 4 to 8 days.

3. The method of claim 1, wherein the EP4 antagonist is selected from the group consisting of an anti-PGE2 antibody, an siRNA against EP4, an shRNA against EP4, a COX-2 antagonist, a mPGES-1 antagonist, GW627368x, AH23848, L-161,982, CJ-023,423, ONO AE3 208, BGC 20-1531 hydrochloride, MF498, and CJ-42794.

4. The method of claim 3, wherein the EP4 antagonist is GW627368x or AH23848.

5. The method of claim 3, wherein an effective amount of the EP4 antagonist is 1.0-40 ug/ml.

6. The method of claim 1, wherein the stem cells are mesenchymal stem cells, mammary epithelial stem cells, or neural stem cells.

7. The method of claim 2, wherein the isolating step includes centrifuging the culture medium containing the stem cells and the exosomes released from the stem cells to obtain a pellet that includes the exosomes.

8. The method of claim 7, wherein the culture medium is centrifuged sequentially at 300 g, 2000 g, 10,000 g, and 110,000 g.

9. The method of claim 1, wherein the higher protein and miRNA content includes one or more of CD44, CD90, integrin β1, integrin α6, N-cadherin, fibronectin, CD146, CD91, cofilin, filamin A, CNP, talin, tropomyosin, galectin 3, Rap1, β-catenin, TGFβ-R1, TGFβ-R2, LRP6, Ago1, Ago2, FZD5, EGFR, HER2, Met, EP2, PI3K, PDK1, Akt, p-Akt, c-Src, p-Src, SAPK/JNK, PSA, VCAM1, VEGFR2, VEGFR3, PDGFβ, NGFR, IL-2Rβ, IL-18Rβ, BMP-7, MIP-3α, RANTES, DR6, LIF, BDNF, TIMP1, VEGFa, IL-10, mir-17-92, mir-106a-363, mir-106b-25 clusters, mir-24, mir-130, mir-17, mir-18a, mir-20a, mir-20b, mir-24, mir-25, mir-29a, mir-106b, mir-130a, and mir-130b.

\* \* \* \* \*